(12) United States Patent
Shelton, IV

(10) Patent No.: US 12,279,837 B2
(45) Date of Patent: Apr. 22, 2025

(54) IDENTIFICATION OF IMAGES SHAPES BASED ON SITUATIONAL AWARENESS OF A SURGICAL IMAGE AND ANNOTATION OF SHAPES OR PIXELS

(71) Applicant: Cilag GmbH International, Zug (CH)

(72) Inventor: Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 131 days.

(21) Appl. No.: 17/747,762

(22) Filed: May 18, 2022

(65) Prior Publication Data

US 2023/0372031 A1    Nov. 23, 2023

(51) Int. Cl.
| | | |
|---|---|---|
| *G16H 30/40* | (2018.01) | |
| *A61B 34/00* | (2016.01) | |
| *A61B 90/00* | (2016.01) | |
| *G16H 20/40* | (2018.01) | |
| *A61B 34/20* | (2016.01) | |

(52) U.S. Cl.
CPC ............ *A61B 34/25* (2016.02); *A61B 90/361* (2016.02); *G16H 20/40* (2018.01); *G16H 30/40* (2018.01); *A61B 2034/2055* (2016.02); *A61B 2090/373* (2016.02)

(58) Field of Classification Search
None
See application file for complete search history.

(56) References Cited

U.S. PATENT DOCUMENTS

| | | |
|---|---|---|
| 9,345,481 B2 | 5/2016 | Hall et al. |
| 10,881,399 B2 | 1/2021 | Shelton, IV et al. |
| 11,589,888 B2 | 2/2023 | Shelton, IV et al. |
| 11,617,492 B2 | 4/2023 | Refai et al. |
| 2014/0263552 A1 | 9/2014 | Hall et al. |
| 2017/0296213 A1 | 10/2017 | Swensgard et al. |
| 2018/0247128 A1* | 8/2018 | Alvi ...................... H04L 67/12 |
| 2019/0200844 A1 | 7/2019 | Shelton, IV et al. |

(Continued)

FOREIGN PATENT DOCUMENTS

| | | |
|---|---|---|
| EP | 1854420 A1 | 11/2007 |
| EP | 3231373 A2 | 10/2017 |

(Continued)

OTHER PUBLICATIONS

Kazanzides, P et al., "Force sensing and 1-40 control for a surgical robot", Proceedings Of The International Conference On Robotics And Automation Nice, France, May 12-14, 1992, pp. 612-617.

*Primary Examiner* — Zaihan Jiang
*Assistant Examiner* — Paramita Ghosh
(74) *Attorney, Agent, or Firm* — Condo Roccia Koptiw LLP

(57) ABSTRACT

Systems, methods, and instrumentalities are disclosed for identification of image shapes based on situational awareness of a surgical image and annotation of shapes or pixels. A surgical video associated with a surgical procedure may be obtained. Surgical context data for the surgical procedure may be obtained. Elements in the video frames may be identified based on the surgical context data using image processing. Annotation data may be determined and generated for the video frames, for example, based on the surgical context data and the identified element(s).

18 Claims, 20 Drawing Sheets

(56) References Cited

U.S. PATENT DOCUMENTS

| | | |
|---|---|---|
| 2019/0200981 A1 | 7/2019 | Harris et al. |
| 2019/0201046 A1 | 7/2019 | Shelton, IV et al. |
| 2019/0201047 A1 | 7/2019 | Yates et al. |
| 2019/0201137 A1 | 7/2019 | Shelton, IV et al. |
| 2019/0201140 A1 | 7/2019 | Yates et al. |
| 2019/0206542 A1 | 7/2019 | Shelton, IV et al. |
| 2019/0206562 A1 | 7/2019 | Shelton, IV et al. |
| 2019/0206569 A1 | 7/2019 | Shelton, IV et al. |
| 2019/0231220 A1 | 8/2019 | Refai et al. |
| 2019/0279765 A1* | 9/2019 | Giataganas ............ G06F 3/014 |
| 2019/0325574 A1* | 10/2019 | Jin ....................... G06V 10/454 |
| 2019/0362834 A1* | 11/2019 | Venkataraman ....... G16H 20/40 |
| 2020/0405403 A1 | 12/2020 | Shelton, IV et al. |
| 2021/0205031 A1 | 7/2021 | Shelton, IV et al. |
| 2021/0298795 A1 | 9/2021 | Bowling et al. |
| 2021/0322017 A1 | 10/2021 | Shelton, IV et al. |
| 2021/0370790 A1 | 12/2021 | Feldman |
| 2022/0108789 A1 | 4/2022 | Shelton, IV et al. |
| 2022/0233119 A1 | 7/2022 | Shelton, IV et al. |
| 2022/0354347 A1 | 11/2022 | Nishimura et al. |
| 2023/0028059 A1 | 1/2023 | Shelton, IV et al. |
| 2023/0079275 A1* | 3/2023 | Wu ........................ G06V 20/46 382/103 |
| 2023/0371950 A1 | 11/2023 | Shelton, IV et al. |
| 2023/0371968 A1 | 11/2023 | Shelton, IV et al. |
| 2023/0372012 A1 | 11/2023 | Harris et al. |
| 2023/0372013 A1 | 11/2023 | Shelton, IV et al. |
| 2023/0372030 A1 | 11/2023 | Shelton, IV et al. |
| 2023/0372031 A1 | 11/2023 | Shelton, IV |
| 2023/0377709 A1 | 11/2023 | Shelton, IV et al. |
| 2023/0377726 A1 | 11/2023 | Shelton, IV et al. |
| 2023/0397969 A1 | 12/2023 | Shelton, IV et al. |
| 2023/0404691 A1 | 12/2023 | Shelton, IV et al. |

FOREIGN PATENT DOCUMENTS

| | | | |
|---|---|---|---|
| EP | 3506287 A1 | 7/2019 | |
| KR | 102013857 B1 * | 8/2019 | ............ G06N 20/00 |
| WO | 2018142277 A1 | 8/2018 | |
| WO | 2019117926 A1 | 6/2019 | |
| WO | 2021049438 A1 | 3/2021 | |

* cited by examiner

IDENTIFICATION OF IMAGES SHAPES BASED ON SITUATIONAL AWARENESS OF A SURGICAL IMAGE AND ANNOTATION OF SHAPES OR PIXELS

CROSS-REFERENCE TO RELATED APPLICATIONS

This application is related to the following, filed contemporaneously, the contents of each of which are incorporated by reference herein:
Ser. No. 17/747,806, filed May 18, 2022, titled METHOD OF CONTROLLING AUTONOMOUS OPERATIONS IN A SURGICAL SYSTEM,
Ser. No. 17/747,726, filed May 18, 2022, titled AUTOMATIC COMPILATION, ANNOTATION, AND DISSEMINATION OF SURGICAL DATA TO SYSTEMS TO ANTICIPATE RELATED AUTOMATED OPERATIONS, and
Ser. No. 17/747,747, filed May 18, 2022, titled AGGREGATION OF PATIENT, PROCEDURE, SURGEON, AND FACILITY PRE-SURGICAL DATA AND POPULATION AND ADAPTATION OF A STARTING PROCEDURE PLAN TEMPLATE.

BACKGROUND

Surgical procedures are typically performed in surgical operating theaters or rooms in a healthcare facility such as, for example, a hospital. Various surgical devices and systems are utilized in performance of a surgical procedure. In the digital and information age, medical systems and facilities are often slower to implement systems or procedures utilizing newer and improved technologies due to patient safety and a general desire for maintaining traditional practices

SUMMARY

Systems, methods, and instrumentalities are disclosed for identification of image shapes based on situational awareness of a surgical image and annotation of shapes or pixels. A surgical video associated with a surgical procedure may be obtained. Surgical context data for the surgical procedure may be obtained. Elements in the video frames may be identified based on the surgical context data using image processing. Annotation data may be determined and generated for the video frames, for example, based on the surgical context data and the identified element(s). The video frames in the surgical video may comprise pixels. The identified element(s) may correspond to a respective group of pixels. The identified element(s) may be separated into sub-elements that comprise the respective element. The sub-elements may be comprised of sub-groups of pixels associated with each sub-element.

The annotation data may be inserted into the video frames. For example, the annotation data may be inserted on a pixel level (e.g., respective annotation data be associated with each pixel and/or group of pixels). For example, the annotation data may include one or more of the following: element identification information, element grouping information, element subgrouping information, element type information, element description information, element condition information, surgical step information, surgical task information, surgical event information, surgical instrument information, surgical equipment information, and/or the like.

The surgical context data may be refined and/or updated based on the surgical video. For example, the surgical context data may be refined and/or updated based on the identified element(s) in a video frame. Element(s) in another video frame may be identified, for example, using the refined and/or updated surgical context data (e.g., using image processing). Annotation data for the second video frame may be determined using the refined surgical context data and the element(s) identified in the second video frame.

Tracking information associated with a surgical video may be determined, for example, by analyzing multiple video frames. Elements identified in a first video frame and elements identified in a second video frame may be used, for example, to determine tracking data. The tracking data may be associated with element behavior, element movement, and/or outcome information (e.g., associated with the elements). The annotation data may include the determined tracking data.

The tracking data and/or information may be verified, for example, using anticipated tracking information. The anticipated tracking information may be obtained, for example, based on the surgical context data and/or a surgical procedure plan. The annotation data may include an indication that indicates whether the elements and/or tracking data is verified. For example, the annotation data may indicate that a subset of the identified elements have been verified. The annotation data may indicate that a subset of the identified elements have not been verified.

Jobs, outcomes, and/or constraints may be determined, for example, for a surgical procedure based on the surgical video. The jobs, outcomes, and/or constraints may be determined based on the surgical context data. Surgical task information associated with a first video frame may be determined using the surgical context data and identified elements in the first video frame. Complication information may be determined associated with the determined surgical task, for example, using the surgical context data, the surgical task information, and the identified elements in the first surgical video frame. Outcome information associated with the surgical task may be determined, for example, based on the surgical context data, the surgical task information, and the complication information.

Change and/or control parameters may be determined for a surgical procedure by analyzing the surgical video. Change and/or control parameters may be determined, for example, based on the surgical task information, complication information, and/or the outcome information. A determination to change parameters associated with a surgical procedure may be performed. Parameter may include parameters associated with operating a surgical instrument, surgical equipment, and/or the like. Based on a determination to change parameters associated with a surgical procedure, change and/or control parameters may be determined. A control signal may be generated. The control signal may include an indication that indicates the determined control parameters. The control signal may be sent to a surgical control system, for example, that send parameter information to surgical systems (e.g., surgical instruments, surgical equipment, and/or the like). The change and/or control parameters may be used to perform the surgical procedure.

DETAILED DESCRIPTION

Figure 1:
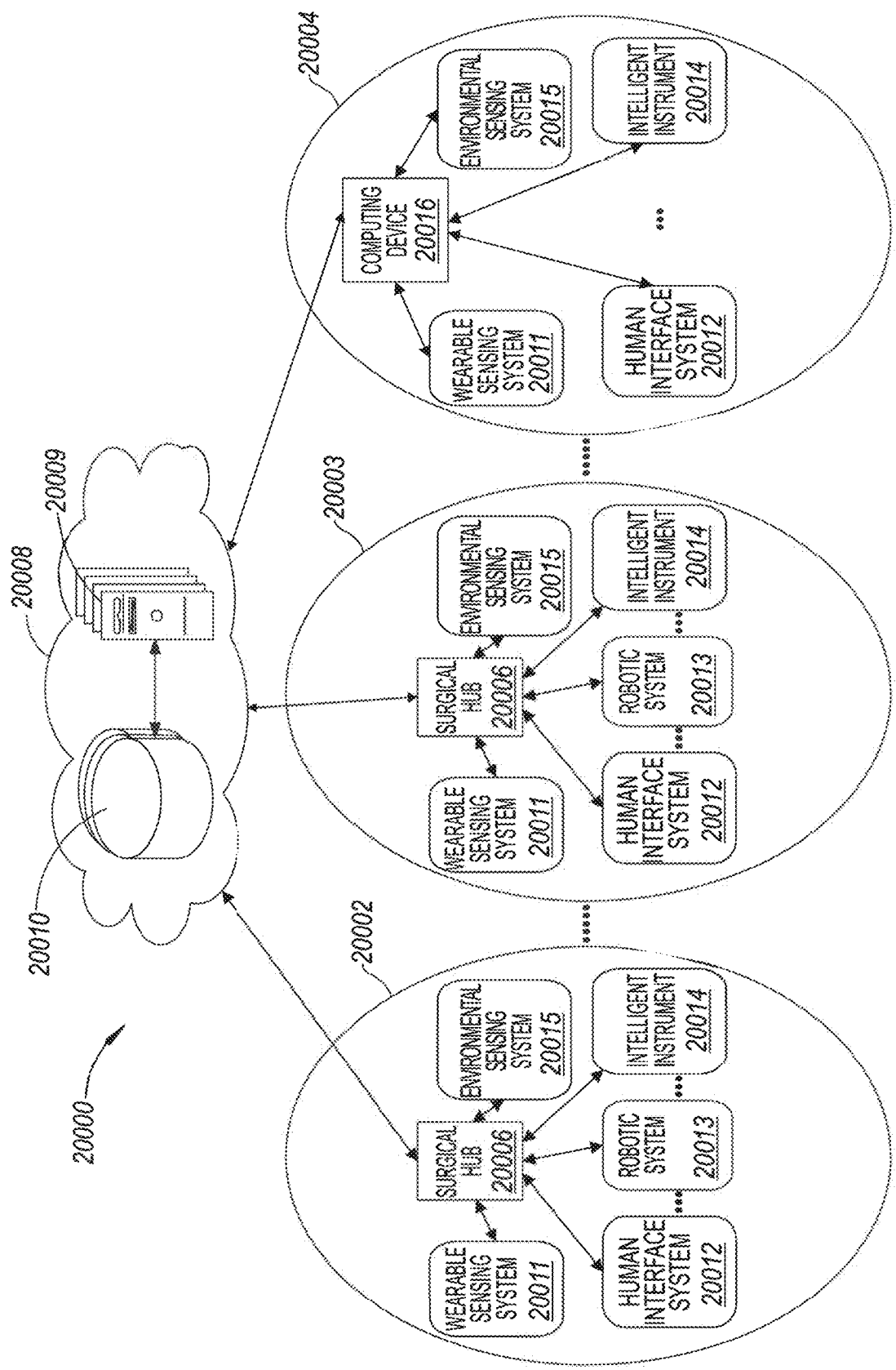
FIG. 1 is a block diagram of a computer-implemented surgical system.

FIG. 1 is a block diagram of a computer-implemented surgical system 20000. An example surgical system such as the surgical system 20000 may include one or more surgical systems (e.g., surgical sub-systems) 20002, 20003 and 20004. For example, surgical system 20002 may include a computer-implemented interactive surgical system. For example, surgical system 20002 may include a surgical hub 20006 and/or a computing device 20016 in communication with a cloud computing system 20008, for example, as described in FIG. 2. The cloud computing system 20008 may include at least one remote cloud server 20009 and at least one remote cloud storage unit 20010. Example surgical systems 20002, 20003, or 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more HCP sensing systems, and/or one or more patient sensing systems. The environmental sensing system 20015 may include one or more devices, for example, used for measuring one or more environmental attributes, for example, as further described in FIG. 2. The robotic system 20013 may include a plurality of devices used for performing a surgical procedure, for example, as further described in FIG. 2.

The surgical system 20002 may be in communication with a remote server 20009 that may be part of a cloud computing system 20008. In an example, the surgical system 20002 may be in communication with a remote server 20009 via an internet service provider's cable/FIOS networking node. In an example, a patient sensing system may be in direct communication with a remote server 20009. The surgical system 20002 and/or a component therein may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

For example, the sensing systems 20001 may include the wearable sensing system 20011 (which may include one or more HCP sensing systems and one or more patient sensing systems) and the environmental sensing system 20015 as discussed in FIG. 1. The one or more sensing systems 20001 may measure data relating to various biomarkers. The one or more sensing systems 20001 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiogramcephalography, colorimetry, impedimentary, potentiometry, amperometry, etc.

The biomarkers measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 20000, for example. The information from the biomarkers may be determined and/or used by the computer-implemented patient and the surgical system 20000 to improve said systems and/or to improve patient outcomes, for example. The one or more sensing systems 20001, biomarkers 20005, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

Figure 2:
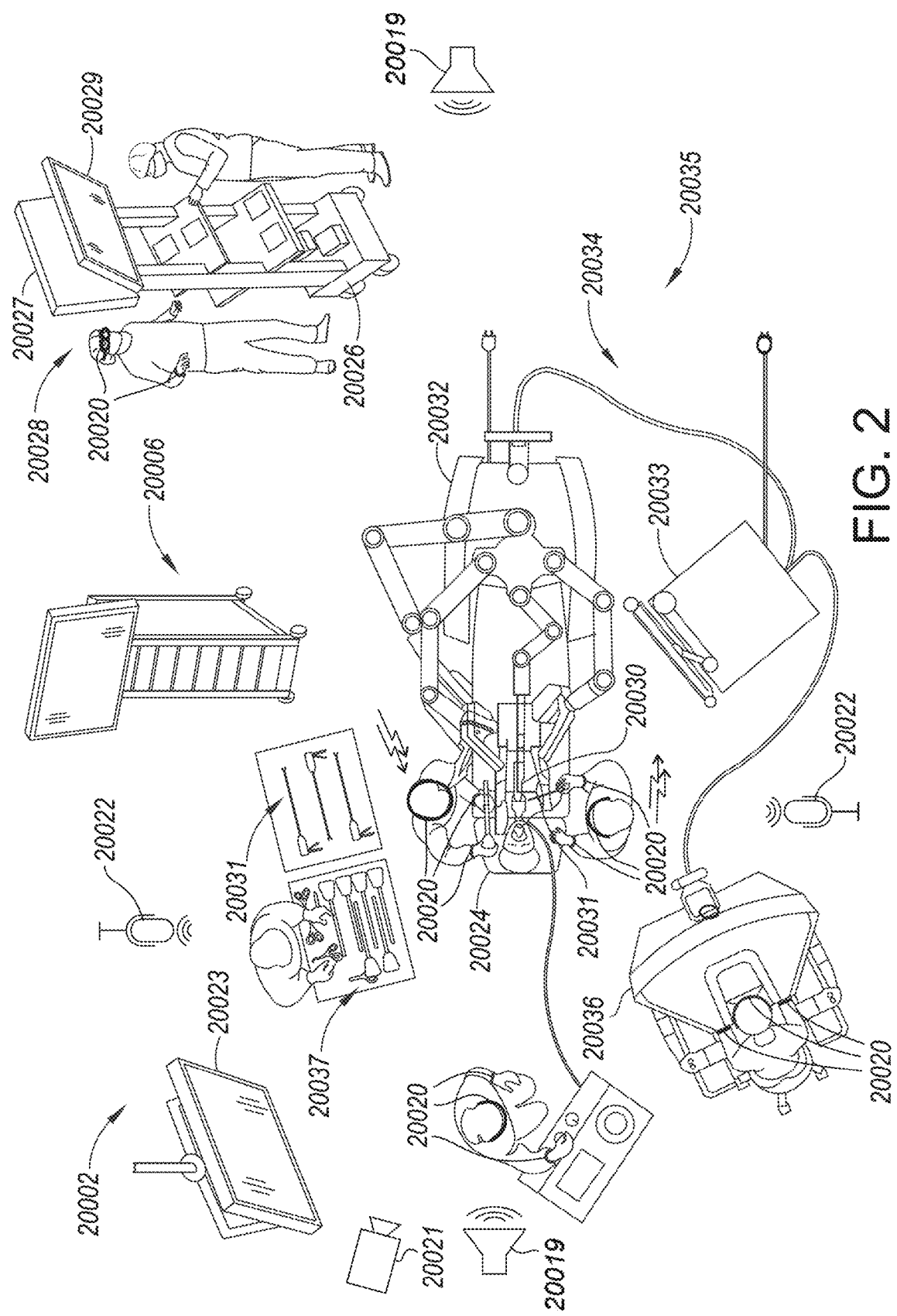
FIG. 2 shows an example surgical system in a surgical operating room.

FIG. 2 shows an example of a surgical system 20002 in a surgical operating room. As illustrated in FIG. 2, a patient is being operated on by one or more health care professionals (HCPs). The HCPs are being monitored by one or more HCP sensing systems 20020 worn by the HCPs. The HCPs and the environment surrounding the HCPs may also be monitored by one or more environmental sensing systems including, for example, a set of cameras 20021, a set of microphones 20022, and other sensors that may be deployed in the operating room. The HCP sensing systems 20020 and the environmental sensing systems may be in communication with a surgical hub 20006, which in turn may be in communication with one or more cloud servers 20009 of the cloud computing system 20008, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2, a surgical instrument 20031 is being used in the surgical procedure as part of the surgical system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1 may include one or more sensing systems, for example, HCP sensing systems 20020 as shown in FIG. 2. The HCP sensing systems 20020 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 20020 may measure a set of biomarkers to monitor the heart rate of an HCP. In an example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 20020 may measure one or more surgeon biomarkers associated with an HCP and send the measurement data associated with the surgeon biomarkers to the surgical hub 20006. The HCP sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 3:
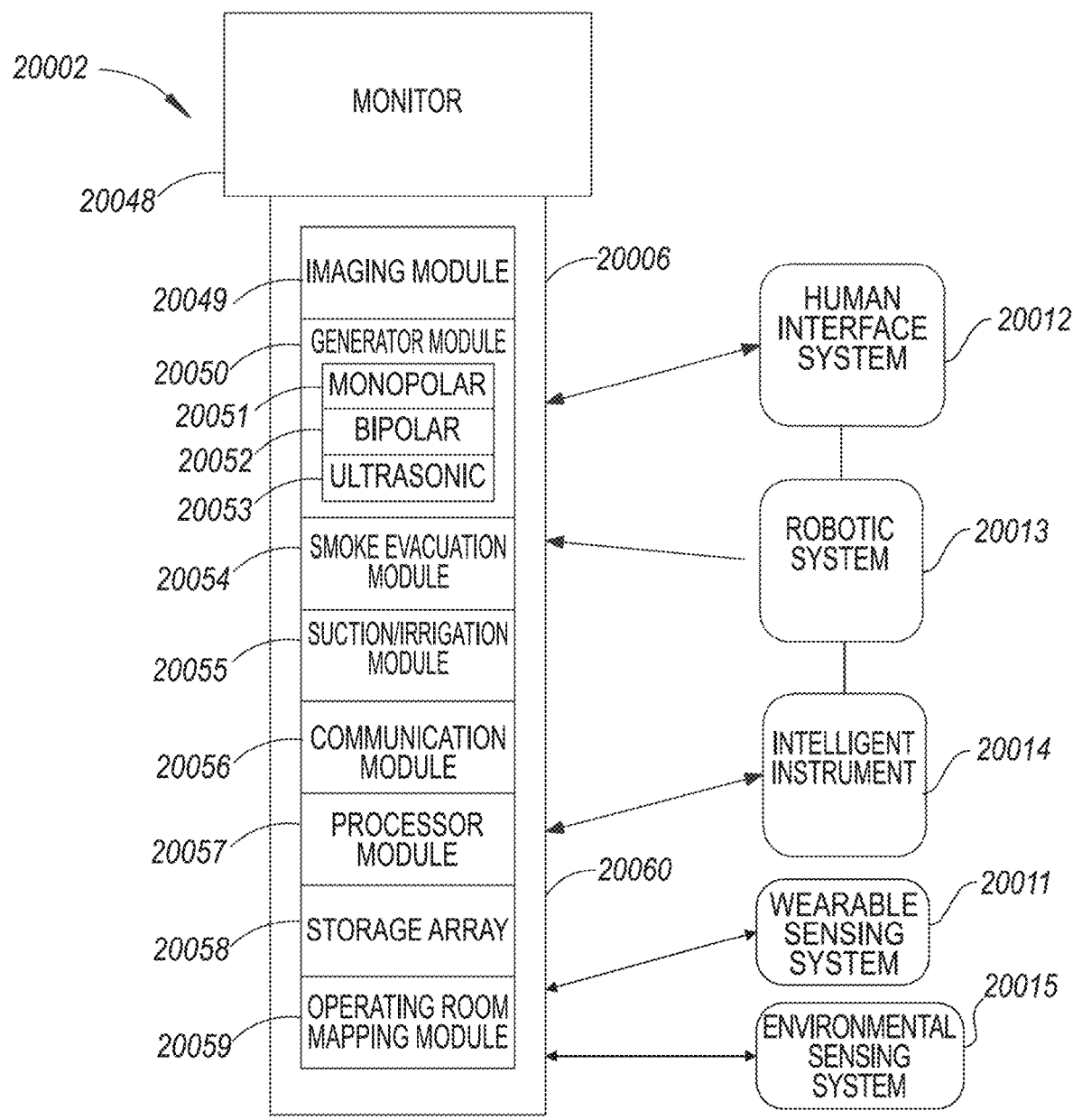
FIG. 3 illustrates an example surgical hub paired with various systems.

FIG. 3 shows an example surgical system 20002 with a surgical hub 20006. The surgical hub 20006 may be paired with, via a modular control, a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. The various modules and systems may be connected to the modular control either directly via a router or via the communication module 20056. The operating theater devices may be coupled to cloud computing resources and data storage via the modular control. The human interface system 20012 may include a display sub-system and a notification sub-system.

The modular control may be coupled to non-contact sensor module. The non-contact sensor module may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
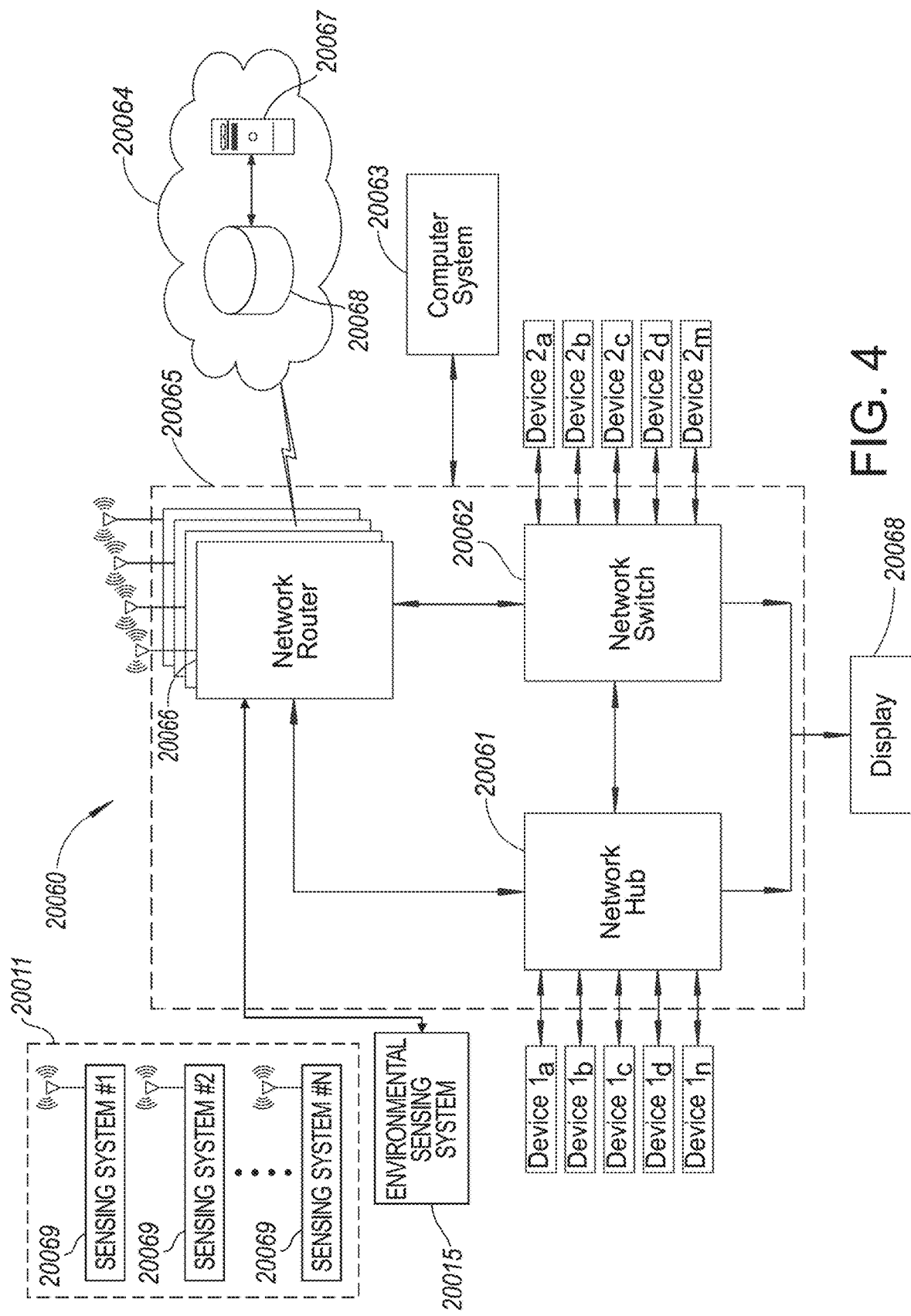
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation.

The computer system 20063 may comprise a processor and a network interface 20100. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 20063 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20063. Data associated with the devices 1a-1n may be transferred to cloud-based computers via the router for remote data processing and manipulation. Data associated with the devices 1a-1n may also be transferred to the local computer system 20063 for local data processing and manipulation. Modular devices 2a-2m located in the same operating theater also may be coupled to a network switch 20062. The network switch 20062 may be coupled to the network hub 20061 and/or the network router 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include an HCP sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m or the sensing systems 20069 to the cloud-base system 20064. One or more of the devices 1a-1n/2a-2m or the sensing systems 20069 coupled to the network hub 20061 or network switch 20062 may collect data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, and notify a patient of a complication during post-surgical period.

The operating theater devices 1a-1n may be connected to the modular communication hub 20065 over a wired channel or a wireless channel depending on the configuration of the devices 1a-1n to a network hub 20061. The network hub 20061 may be implemented, in one aspect, as a local network broadcast device that works on the physical layer of the Open System Interconnection (OSI) model. The network hub may provide connectivity to the devices 1a-1n located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1a-1n can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2a-2m may be connected to a network switch 20062 over a wired channel or a wireless channel. The network switch 20062 works in the data link layer of the OSI model. The network switch 20062 may be a multicast device for connecting the devices 2a-2m located in the same operating theater to the network. The network switch 20062 may send data in the form of frames to the network router 20066 and may work in full duplex mode. Multiple devices 2a-2m can send data at the same time through the network switch 20062. The network switch 20062 stores and uses MAC addresses of the devices 2a-2m to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1a-1n/2a-2m and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and/or the sensing systems 20069 and may handle a data type known as frames. Frames may carry the data generated by the devices 1a-1n/2a-2m and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
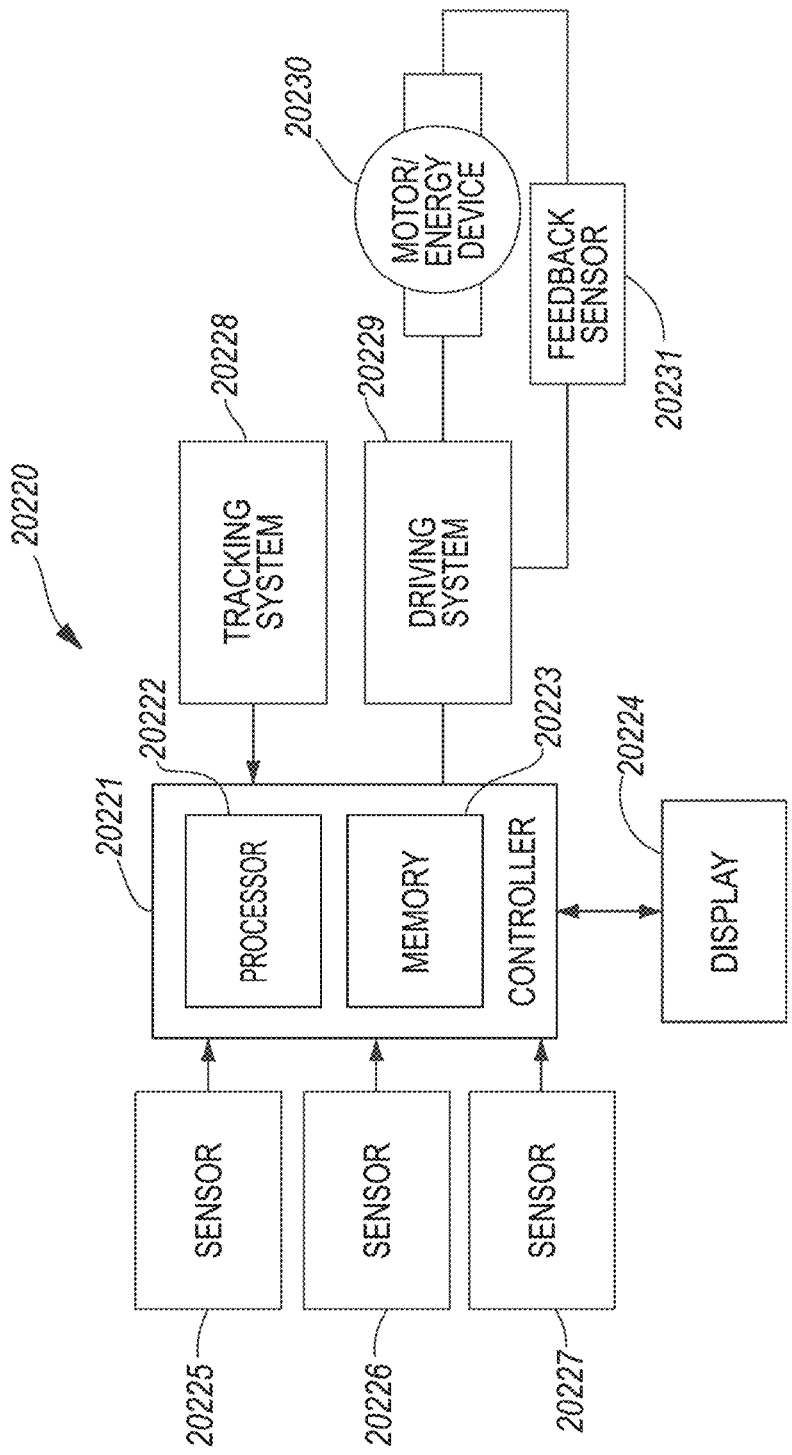
FIG. 5 illustrates a logic diagram of a control system of a surgical instrument.

FIG. 5 illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

The microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

The position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

For example, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the surgical hub 20065 as shown in FIG. 4.

Figure 6:
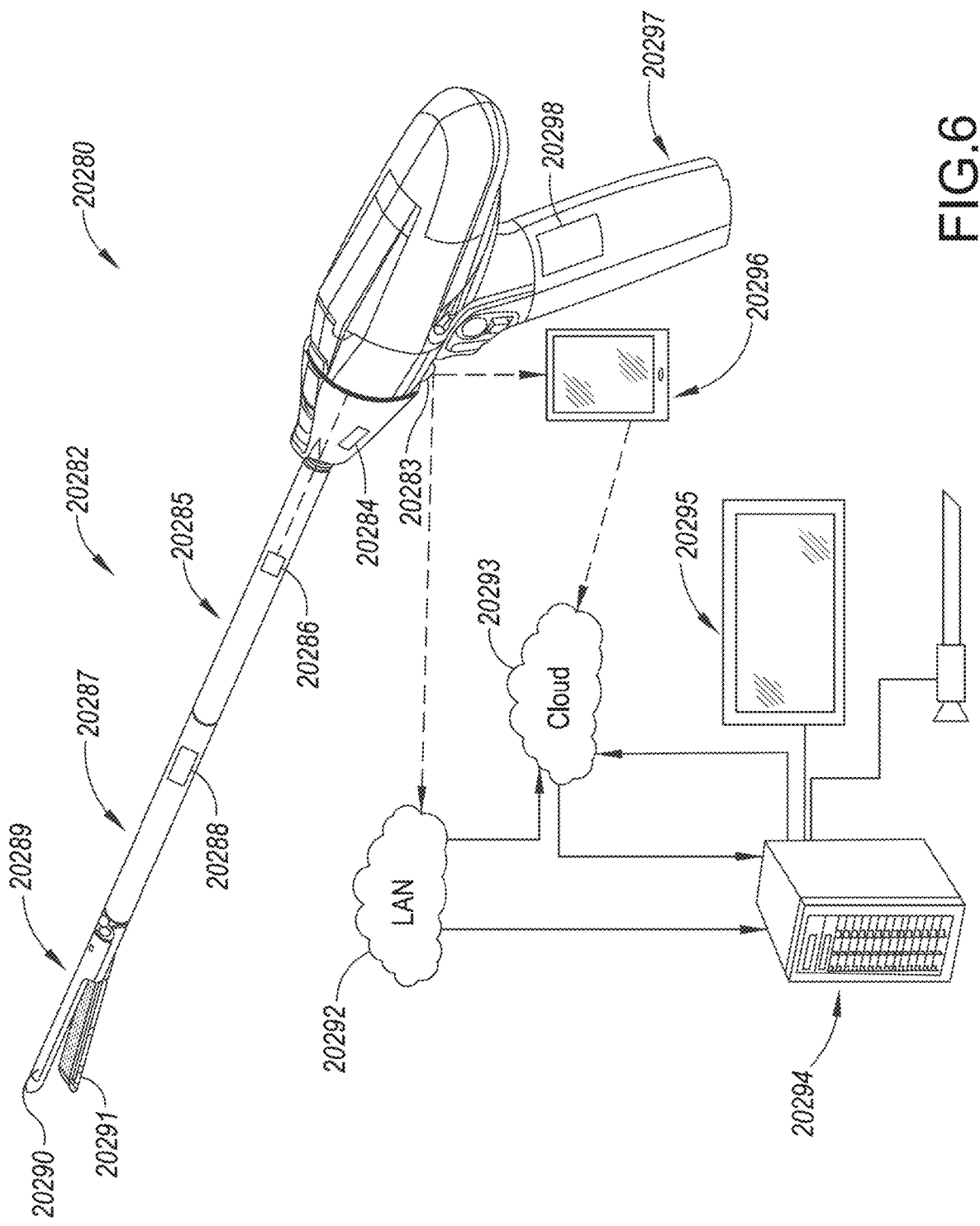
FIG. 6 shows an example surgical device that includes a handle having a controller and a motor, an adapter releasably coupled to the handle, and a loading unit releasably coupled to the adapter.

FIG. 6 illustrates an example surgical system 20280 in accordance with the present disclosure and may include a surgical instrument 20282 that can be in communication with a console 20294 or a portable device 20296 through a local area network 20292 and/or a cloud network 20293 via a wired and/or wireless connection. The console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 7:
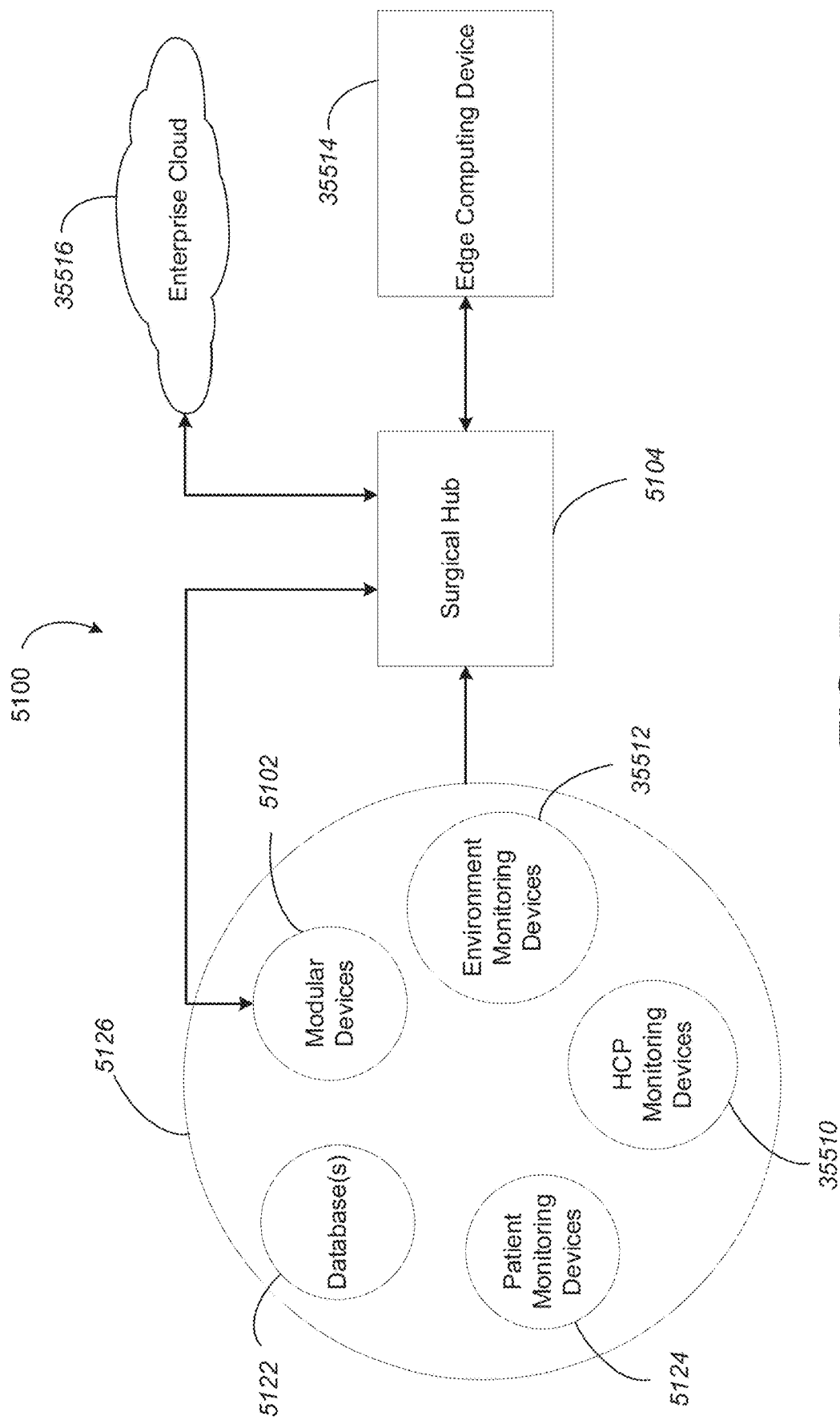
FIG. 7 shows an example situationally aware surgical system.

FIG. 7 illustrates a diagram of a situationally aware surgical system 5100, in accordance with at least one aspect of the present disclosure. The data sources 5126 may include, for example, the modular devices 5102 (which can include sensors configured to detect parameters associated with the patient, HCPs and environment and/or the modular device itself), databases 5122 (e.g., an EMR database containing patient records), patient monitoring devices 5124 (e.g., a blood pressure (BP) monitor and an electrocardiogramonitor), HCP monitoring devices 35510, and/or environment monitoring devices 35512. The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." For example, the surgical hub 5104 can incorporate a situational awareness system, which is the hardware and/or programming associated with the surgical hub 5104 that derives contextual information pertaining to the surgical procedure from the received data and/or a surgical plan information received from the edge computing system 35514 or an enterprise cloud server 35516.

The situational awareness system of the surgical hub 5104 can be configured to derive the contextual information from the data received from the data sources 5126 in a variety of different ways. For example, the situational awareness system can include a pattern recognition system, or machine learning system (e.g., an artificial neural network), that has been trained on training data to correlate various inputs (e.g., data from database(s) 5122, patient monitoring devices 5124, modular devices 5102, HCP monitoring devices 35510, and/or environment monitoring devices 35512) to corresponding contextual information regarding a surgical procedure. A machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (e.g., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (e.g., whether bleeding at a surgical site has stopped) according to video or image data received from a medical imaging device. The surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. The situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use as soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could proactively change the displayed view (supplied by, e.g., a medical imaging device for the visualization system) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can compare the list of items for the procedure and/or a list of devices paired with the surgical hub 5104 to a recommended or anticipated manifest of items and/or devices for the given surgical procedure. If there are any discontinuities between the lists, the surgical hub 5104 can provide an alert indicating that a particular modular device 5102, patient monitoring device 5124, HCP monitoring devices 35510, environment monitoring devices 35512, and/or other surgical item is missing. In some examples, the surgical hub 5104 can determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other HCP(s)) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. The surgical hub 5104 can provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Enormous amounts of surgical data are generated during surgical procedures. Surgical tasks performed during and/or after the surgical procedure are continually completed using the generated surgical data. Surgical systems may request specific task-related data for a surgical task before performing the task or the surgical systems may receive the wholesale surgical data and may parse through the complete dataset to find the specific task-related data needed for the task. This may create a delay or use unnecessary resources in performing the surgical task. Parsing through wholesale surgical procedure data to find task-specific data for a task is inefficient and poses a bandwidth problem as wholesale data is communicated to a surgical system that only needs a portion of the data.

Systems, methods, and instrumentalities are disclosed for automatic compilation, annotation, and dissemination of surgical data to surgical systems and/or devices to anticipate (e.g., in advance of, before, in preparation for) related automated operations. A surgical computing system may be configured to obtain data (e.g., surgical procedure data) associated with, for example, a patient being treated in the operating room, healthcare professionals (HCPs) participating in the surgical procedure, the surgical devices and/or equipment used in the surgical procedure, surgical sensors, a surveillance system in the operating room, a surgical hub, and/or the like. The surgical procedure data may be compiled, for example, by a surgical computing system. The surgical computing system may be configured to annotate the surgical procedure data. The annotations may indicate a surgical context and/or a surgical procedure step. The surgical computing system may identify surgical systems, for example, that may use the annotated data for related surgical tasks. The surgical computing system may determine data needs (e.g., data to be used for a task) for an identified surgical system (e.g., target surgical system). The computing system may generate selectively discriminated data (e.g., a data package, a data stream) for the target surgical system, for example, by decompiling the annotated surgical procedure data. The selectively discriminated data may include at least a portion of the annotated surgical procedure data (e.g., complete annotated surgical procedure data). The surgical computing system may send the selectively discriminated data to the target surgical system, for example, for the target surgical system to use in a subsequent task.

The surgical computing system may determine the data needs for the target surgical system based on the surgical procedure data, for example, using situational awareness (e.g., as described herein with respect to FIG. 7). The surgical computing system may determine a current surgical context and/or a current surgical procedure step in the surgical procedure, for example, based on the surgical procedure data. Based on the current surgical context and/or current surgical procedure step, the surgical computing system may determine a subsequent surgical context and/or subsequent surgical procedure step (e.g., the next surgical context and/or surgical procedure step to occur after the current surgical context and/or surgical procedure step). The surgical computing system may determine tasks associated with the subsequent surgical context and/or subsequent surgical procedure step to be performed by surgical systems. The surgical computing system may determine the data needs based on the determined tasks associated with the subsequent surgical context and/or subsequent surgical procedure step. For example, the surgical computing system may anticipate the data to be used for the tasks in the subsequent surgical context and/or subsequent surgical procedure step.

The surgical computing system may perform selective redaction on the surgical procedure data, annotated surgical procedure data, and/or data package. The surgical computing system may perform redaction, for example, on pre-identified data and/or conditional aspects of the data. For example, the surgical computing system may perform redaction on confidential aspects of the surgical procedure data (e.g., in accordance with the Health Insurance Portability and Accountability Act (HIPAA)). Redaction may include removing confidential aspects of the surgical procedure data, for example, by removing the confidential data, replacing the data (e.g., with generic and/or default values), scramble, encrypt, and/or the like to render the confidential aspects unreadable. The surgical computing system may redact unusual and/or unexpected data. The redaction may be temporally and/or geo-fence controlled.

Figure 8:
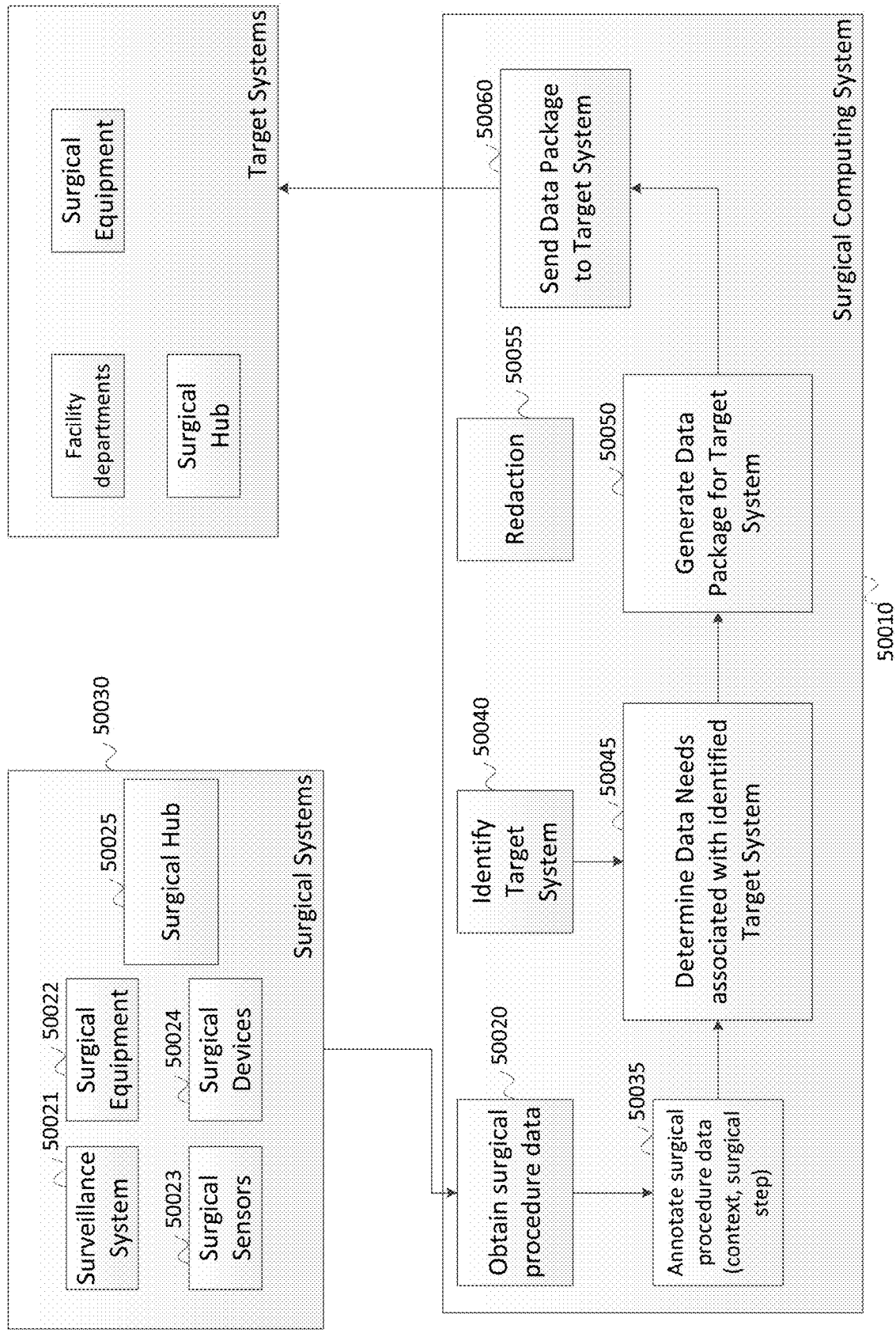
FIG. 8 illustrates an example flow diagram of a surgical computing system automatically performing selective dissemination of annotated surgical procedure data to surgical systems.

FIG. 8 illustrates an example flow diagram of a surgical computing system automatically performing selective dissemination of annotated surgical procedure data to surgical systems. As shown in FIG. 8 at 50020, a surgical computing system 50010 may obtain surgical procedure data. The surgical procedure data may be obtained from the surgical systems 50030, for example. At 50035, the surgical computing system 50010 may annotate the surgical procedure data. As shown at 50040 in FIG. 8, the surgical computing system 50010 may identify/determine a target system (e.g., target surgical system). At 50045, the surgical computing system 50010 may determine data need(s) associated with the target system. The data needs may be associated with a task, for example, to be performed by the target system (e.g., in a subsequent/future/next surgical step). The data needs may be associated with the data used (e.g., required) in performing the task. As shown at 50050, the surgical computing system 50010 may generate a data package (e.g., a data stream), for example, for the target system. The data package may be generated based on the annotated surgical procedure data and/or the data needs associated with the target system. As shown at 50055, the surgical computing system 50010 may be configured to perform redaction. The redaction may be performed on the obtained surgical procedure data, the annotated surgical procedure data, the data package, and/or the like. At 50060, the surgical computing system 50010 may send the data package to the target system. The target system may be for example a surgical hub, a surgical instrument, surgical equipment, systems associated with a facility department, a billing system, and/or the like.

The surgical computing system 50010 may obtain surgical procedure data, for example, from systems/devices in the surgical systems 50030. For example, the surgical computing system 50010 may obtain surgical procedure data from one or more of a surveillance system 50021, surgical equipment 50022, surgical sensors 50023, surgical devices 50024, surgical hub(s) 50025, and/or the like.

The surgical procedure data may be data associated with a surveillance system, a surgical sensor (e.g., biomarker sensor, HCP sensor, etc.) surgical equipment, surgical devices, surgical tools, staffing for a surgical procedure, OR setup/layout, surgical procedure steps, consumables used for a surgical procedure, electronic medical records, imaging scans and/or results, surgical outcomes, and/or the like. For example, the surgical procedure data may include raw data from the surgical systems the data is obtained from. The surgical procedure data may be processed data (e.g., from the surgical hub 50025). For example, the surgical hub 50025 may process obtained surgical sensor data. The processed raw data may indicate surgical events, surgical procedure steps, timing, surgical outcomes, device utilization, and/or the like. The surgical computing system 50010 may obtain the processed surgical procedure data.

The surgical computing system 50010 may compile the obtained surgical procedure data. In examples, the surgical computing system 50010 may obtain compiled surgical procedure data. For a surgical procedure, the surgical hub 50025 may obtain data from the surgical systems (e.g., operating room (OR)) that the surgical hub is associated with. The surgical hub 50025 may compile the obtained surgical procedure data and send the compiled surgical procedure data to the surgical computing system 50010. The surgical computing system 50010 may use the obtained compiled surgical procedure data for annotation and/or dissemination to target systems.

The surgical computing system 50010 may annotate the surgical procedure data (e.g., compiled surgical procedure data). For example, the surgical computing system 50010 may annotate the surgical procedure data based on situational awareness (e.g., as described herein with reference to FIG. 7). The surgical computing system 50010 may determine surgical context data, which may indicate a surgical event, a time, a surgical procedure step, and/or the like, for example, based on the surgical procedure data. The annotations may be associated with the determined surgical context, surgical event, time, surgical procedure step, and/or the like. The annotations may be used to give context to the surgical procedure data, for example, if the surgical procedure data is decompiled.

As shown at 50040, the target system(s) may be identified. For example, the target systems may include surgical systems (e.g., in the OR and/or in the facility), facility department systems, surgical equipment, surgical hubs, a billing system and/or the like. The target systems may be performing tasks (e.g., surgical tasks) associated with the surgical procedure. For example, target systems (e.g., facility department systems) may be configured to schedule replacement, repair, and/or cleanup of an OR and consumables (e.g., materials used during the surgical procedure).

The target systems may use surgical procedure data to perform the tasks. For example, a surgical task in a subsequent surgical procedure step may be performed autonomously, based on surgical procedure data associated with earlier surgical tasks and/or surgical procedure steps. For example, a surgical procedure data associated with a first surgical procedure step may be used by a target system to perform a surgical task in a second surgical procedure step. For example, surgical procedure data may include patient surgical sensor data associated with a patient biomarker. The patient biomarker information may be used by a target system to perform a surgical task in a subsequent surgical procedure step/phase. For example, the target system may alter parameters associated with the task based on the patient biomarker information.

At 50045, the surgical computing system 50010 may determine data need(s) associated with the identified target system. The data needs may be a set of data used (e.g., by the target system) to perform a surgical task. The surgical computing system 50010 may determine the data needs based on the surgical task the surgical system is configured to perform (e.g., configured to perform at a later time or subsequent surgical step). For example, the data needs may be anticipated by the surgical computing system 50010.

The surgical computing system 50010 may determine (e.g., anticipate) the task (e.g., to be performed by the target system) based on situational awareness, for example, using the surgical procedure data and/or annotated surgical procedure data. For example, the surgical computing system 50010 may determine a current surgical context and/or surgical procedure step based on the surgical procedure data. Using the current surgical context and/or surgical procedure step, a subsequent surgical context and/or surgical procedure step may be determined. The subsequent surgical context and/or surgical procedure step may be determined (e.g., anticipated) using a surgical procedure plan and the current surgical context and/or surgical procedure step.

For example, the surgical computing system may determine (e.g., based on the surgical procedure data), that the surgical procedure is currently in a first surgical procedure step. The surgical computing system may identify a second surgical procedure step as the surgical procedure step that follows the first surgical procedure step in the surgical procedure plan. The surgical computing system may determine surgical tasks associated with the second surgical procedure step. With the knowledge of the surgical tasks, data needs associated with the surgical tasks may be determined. The surgical computing system may anticipate the data needs before the second surgical procedure step occurs. The surgical computing system may determine the data needs associated with the target surgical system, for example, without the target system sending a request indicating the data needs.

Various examples of surgical steps and corresponding data needs, and are suitable for use with the present disclosure, are described in U.S. patent application Ser. No. 17/156,287, titled METHOD OF ADJUSTING A SURGICAL PARAMETER BASED ON BIOMARKER MEASUREMENTS, filed on Jan. 22, 2021, the disclosure of which is herein incorporated by reference in its entirety. For example, a thoracic surgery may be performed, such as a lung lobectomy. A surgical computing system may determine that the lung lobectomy is in a surgical step associated with managing major vessels. The surgical computing system may determine that the surgical procedure is in the major vessel management step, for example, based on surgical procedure data (e.g., determining a current surgical task associated with the major vessel management step is being performed). For example, the surgical computing system may determine that the current surgical task is ligating a patient's pulmonary artery (e.g., based on the surgical procedure data). The surgical computing system may determine that the lobe removal surgical step is a subsequent surgical step (e.g., the next surgical step) in the lung lobectomy. The surgical computing system may determine that the lobe removal surgical step follows the major vessel management step. The surgical computing system may determine that the lobe removal step includes using a surgical stapler (e.g., linear stapler) for a surgical task. For example, the surgical stapler may be used in a surgical task associated with transecting a fissure. The surgical stapler may be adaptively controlled, for example, using dynamic parameters for operating the surgical stapler based on the surgical procedure data. Surgical procedure data from previous surgical procedure steps and/or tasks may be used to determine the parameters used for operating the surgical stapler. The surgical computing system may determine the data needs of the surgical stapler used in the fissure transection. The surgical computing system may selectively discriminate the data that may be used for the fissure transection from the surgical procedure data. The surgical computing system may send the selectively discriminated data to surgical stapler, for example, in anticipation of the task (e.g., before the surgical step involving the surgical stapler). The selectively discriminated data may be sent to the surgical stapler, for example, before a request for the specific data is received.

A data package/stream (e.g., comprising selectively discriminated data) may be generated, for example, for the target system. The surgical computing system 50010 may generate the data package/stream for the target system using the annotated surgical procedure data based on the determined data needs associated with the target system. The data package/stream may be generated, for example, using automated selective discrimination (e.g., selecting portions of the annotated surgical procedure data set for dissemination to the appropriate systems). For example, the data package/stream may include data relevant to the data needs and exclude data not used by the target system. Automated selective discrimination may enable sending discrete chunks of data (e.g., rather than wholesale communication of all the compiled surgical procedure data) to communicate with target systems. Automated selective discrimination may minimize bandwidth issues and/or storage issues.

In examples, the surgical computing system may select a portion of the annotated surgical procedure data to generate the data package/stream. The surgical computing system may decompile the associated data from the complete set of annotated surgical procedure data. The decompiled data may be tagged (e.g., time tagged) using situational awareness and/or the surgical context. The portion of the annotated surgical procedure data may be a subset of complete set of annotated surgical procedure data. For example, the data package/stream may include a sub-set of procedure steps, a subset of resources used in the surgical procedure (e.g., consumables used, costs, time logged, etc.), redacted information, and/or the like.

The surgical computing system 50010 may perform redaction on the surgical procedure data. For example, the surgical computing system 50010 may perform redaction on the surgical procedure data (e.g., the obtained surgical procedure data), the annotated surgical procedure data (e.g., based on the annotation), the data package/stream, and/or the like.

At 50060, the data package/stream may be sent to the target system. The target system may include surgical systems, facility systems, and/or the like. For example, the target system may include a device maintenance scheduling system (e.g., for determining when to service/repair a surgical tool/device). The target system may include a surgical hub that is performing a surgical procedure. The surgical hub may obtain the data package/stream and use the data package/stream for subsequent surgical procedure steps.

In examples, the computing system may perform automated selective discrimination of data sets (e.g., automatically annotated datasets) and may send (e.g., disseminate) specific data packages to different systems. The computing system may send data packages containing data associated with the data needs of the target systems. The computing system may decompile obtained surgical procedure data and annotate the decompiled data (e.g., with a surgical context and/or time tags, for example, using situational awareness). The computing system may send the decompiled data (e.g., discrete chunks of data) to a target system. The computing system may refrain from sending the compiled surgical procedure data (e.g., entire set of surgical procedure data) by sending (e.g., only sending) the decompiled data. Sending the decompiled data may minimize bandwidth issues and/or storage issues.

In examples, the decompiled data (e.g., select packets of data) may be separated. The decompiled data packets may be separated based on a characterization, a risk level, a prioritization, a magnitude of change from the expected (e.g., outlier data), hierarchical segmentation, system utilization, and/or the like.

In examples, the surgical procedure data may be used during the automated selective discrimination (e.g., as described herein). For example, if a portion of surgical procedure data is different (e.g., significantly different and/ or different beyond a threshold value) than as expected, the portion of surgical procedure data that is different (e.g., outlier data, unexpected data) may be included in the data package. For example, the surgical computing system may obtain statistical data associated with the performed surgical procedure. The statistical data may include expected and/or average data. The statistical data may include expected deviations (e.g., thresholds) associated with the expected and/or average data. The surgical computing system may determine that surgical procedure data deviates from the expected and/or average data, for example, beyond a threshold. The surgical computing system may flag the surgical procedure data, and the flag may indicate the deviation. In examples, the portion of surgical procedure data that is different (e.g., deviant from expected values) may be tagged with an indication (e.g., indicating that it is different from expected). A computing system may include in the data package surgical procedure data that makes up a threshold amount of data (e.g., disproportionate amount of the data). The surgical procedure data that makes up a threshold amount of data may be tagged with an indication (e.g., indicating that the data makes up the threshold amount of data).

Figure 9:
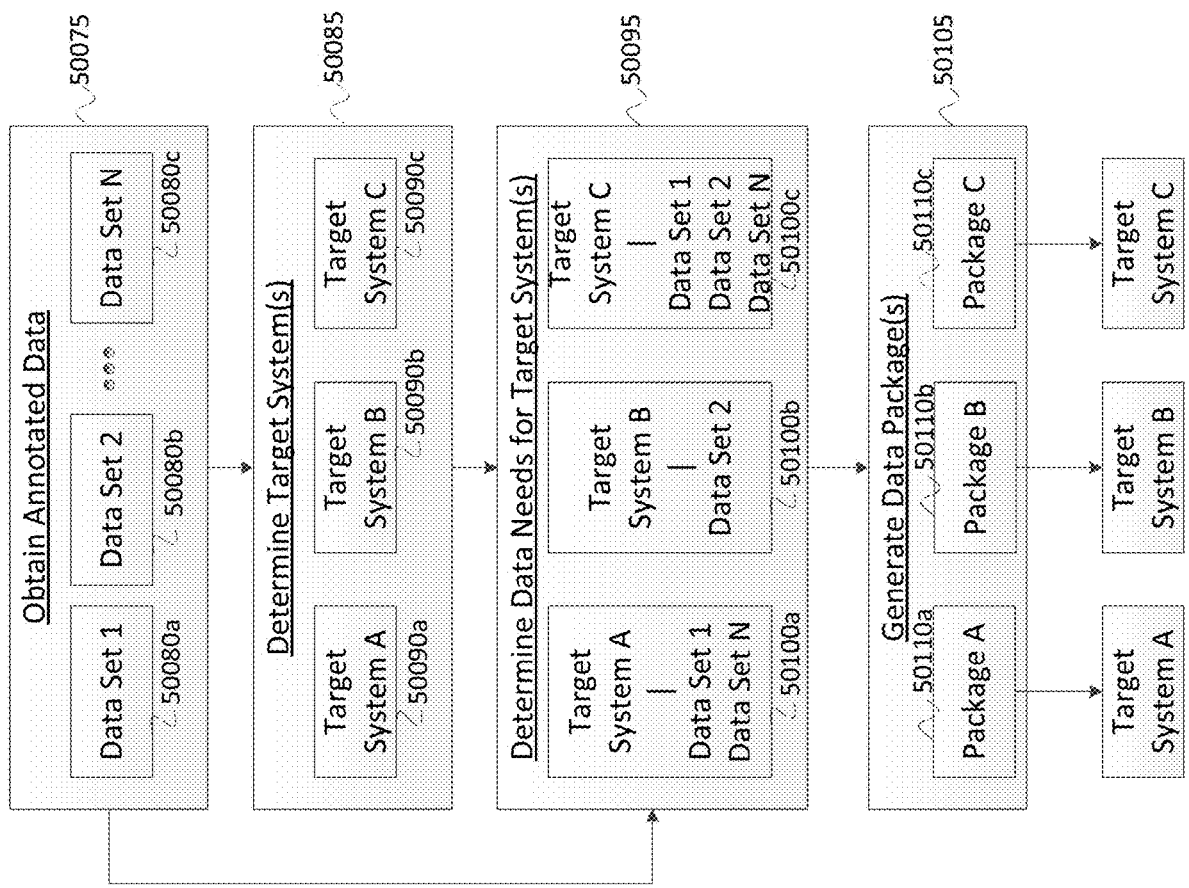
FIG. 9 illustrates an example of generating and sending data packages to target systems.

FIG. 9 illustrates an example of generating and sending data packages to target systems. Surgical procedure data (e.g., compiled surgical procedure data) may be obtained. The surgical procedure data may include the data (e.g., all the data) associated with the surgical procedure. Target systems may use portions of the surgical procedure data, for example, to perform surgical tasks. The target systems may not need or require the entire compiled surgical procedure data. Sending the compiled surgical procedure data (e.g., entire set of surgical procedure data) may cause unnecessary bandwidth and/or storage issues.

As shown in FIG. 9 at 50075, surgical procedure data may be obtained. The obtained surgical procedure data may be annotated, and or annotation may be performed on the obtained surgical procedure data. The annotated surgical procedure data may include datasets (e.g., multiple datasets), such as, for example, Data Set 1 50080*a*, Data Set 2 50080*b*, Data Set N 50080*c*, etc.

As shown at 50085, the target system(s) may be determined/identified. The target system(s) may include systems that receive surgical procedure data to perform tasks, such as, for example, surgical tasks, data storage, facility management, and/or the like. Target system(s), such as Target System A 50090*a*, Target System B 50090*b*, and/or Target System C 50090*c* may be determined/identified by the surgical computing system. For example, the target system(s) may be identified based on the current surgical context (e.g., current surgical procedure step). The target system(s) may be identified as performing tasks, for example, in the current surgical context and/or a subsequent surgical context.

As shown at 50095, data needs may be determined for the target system(s). Different target systems may be associated with different data needs. For example, a first data needs may be associated with Target System A 50090*a*. As shown at 50100*a*, the first data needs may be associated with Data Set 1 50080*a* and/or Data Set N 50080*c*. A second data needs may be associated with Target System B 50090*b*. As shown at 50100*b*, the second data needs may be associated with Data Set 2 50080*b*. A third data needs may be associated with Target System C 50090*c*. As shown at 50100*c*, the third data needs may be associated with Data Set 1 50080*a*, Data Set 2 50080*b*, and/or Data Set N 50080*c*. The data needs may be determined, for example, based on the annotated surgical procedure data (e.g., as described herein).

As shown at 50105, the data package(s) may be generated. The data package(s) may be generated for the target system(s). The data package(s) may include data associated with the data needs (e.g., only data associated with the data needs) for the target system(s). The target system(s) may receive a portion of the surgical procedure data (e.g., a portion of the complete version of the annotated surgical procedure data). For example, the data package may include redacted information, a sub-set of the procedure steps, and/or a subset of data collected (e.g., consumables used, costs, time logged, etc.).

As shown in FIG. 9, a generated Package A 50110*a* may include data associated with the data needs associated with Target System A 50090*a*. For example, Package A 50110*a* may include Data Set 1 50080*a* and/or Data Set N 50080*c*. A generated Package B 50110*b* may include data associated with the data needs associated with Target System B 50090*b*. For example, Package B 50110*b* may include Data Set 2 50080*b*. A generated Package C 50110*c* may include data associated with the data needs associated with Target System C 50090*c*. For example, Package C 50110*c* may include Data Set 1 50080*a*, Data Set 2 50080*b*, and/or Data Set N 50080*c*. The data packages may be sent to the target system(s).

Redaction may be performed on surgical procedure data. The redaction may be performed on the compiled surgical procedure data, annotated surgical procedure data, data packages, individual data sets, and/or the like. Redaction may be performed more than once. Selective redaction may be automated. For example, selective redaction may be automated based on pre-identified and/or conditional aspects of the data. For example, surgical contexts, events, images, datasets, etc. may be used (e.g., as a filter) to select portions of the data for removal. Portions of the data may be selected for removal and may be redacted from generated data packages.

For example, pre-defined portions of surgical procedure data may follow a set of rules for inclusion and/or exclusion in data packages. Data may be redacted based on satisfying a condition of exclusion from the data set. A portion of data within a dataset may be redacted (e.g., only a portion of the dataset may be redacted). Data may be redacted, for example, if it is associated with confidential information (e.g., HIPAA information). Data may be redacted, for example, if the data is unusual and/or unexpected (e.g., different from an expected value beyond a threshold value). The data may be flagged as unusual and/or unexpected (e.g., but not redacted). Data may be redacted, for example, based on temporal conditions and/or location conditions (e.g., geo-fenced controlled). For example, conditions for redacting data may be associated with one or more of the following: whether an amount of time has passed; when the data leaves the network/system; when the surgical procedure is completed; if the data is transferred to a protected archive; and/or the like. For example, the data may be redacted after (e.g., only after) a predetermined amount of time has passed.

Redacted data may be flagged, for example, such as tagged with an indication indicating that the data is redacted. The redacted data may be flagged such that it indicates that the information is to be removed (e.g., automatically removed). The redacted data may be flagged such that it indicates the condition(s) associated with the redaction.

For example, redaction may be performed on data based on a classification. For example, a classification may be determined for surgical procedure data (e.g., a portion of surgical procedure data). For example, surgical procedure data may include private and/or confidential information (e.g., according to HIPAA guidelines). The surgical computing system may determine a private classification for surgical procedure data that includes private and/or confidential information. Redaction may be performed on surgical procedure data determined to have a private classification. The surgical computing system may refrain from performing redaction on surgical procedure data that does not include private and/or confidential information.

For example, redaction may be performed on data based on a target system (e.g., to which the data is to be sent). Surgical procedure data may be redacted based on a classification associated with the surgical procedure data and the target system. For example, a target system may be a surgical system within or outside of a patient privacy protection boundary. The target system may be a surgical system at a geographic location, a network-based location, or organization-based location, which may indicate whether the system is inside or outside of the patient privacy protection boundary. The geographic location may be outside the HIPAA boundary. The surgical computing system may determine to redact surgical procedure data classified as private information based on the target system's geographic location (e.g., because it is outside the HIPAA boundary). Confidential information (e.g., with respect to HIPAA) may not be permitted to be sent outside the HIPAA boundary. The target system may be a surgical system at a geographical location within the HIPAA boundary. The surgical computing system may determine to refrain from redacting surgical procedure data classified as private information. For example, a data storage may be located in the cloud network (e.g., outside the HIPAA boundary). The surgical computing system may redact confidential information before sending data to the cloud network data storage. For example, a patient's electronic medical record storage may be located in a facility (e.g., within the HIPAA boundary). The surgical computing system may refrain from performing redaction before sending the data to the patient's electronic medical record storage.

In examples, a computing system may annotate (e.g., automatically annotate) surgical procedure data (e.g., video feeds) during a surgical procedure. The annotations may indicate surgical step(s) and/or time scales associated with the surgical procedure. The computing system may flag aspects of the annotation (e.g., and/or the video feed) in different coding aspects. For example, a first coding aspect may be associated with the computing system maintaining the integrated surgical procedure data (e.g., video feed) as whole. A second coding aspect may be associated with the computing system redacting data after a secure storage (e.g., primary secure storage) of the surgical procedure is completed (e.g., after the surgical procedure ends). A third coding aspect may be associated with the computing system redacting portions of data (e.g., aspects of the data) before transmission of the data packages to the target systems (e.g., after the data packages leave the primary secure storage).

In examples, the secure storage may be configured with an amount of time. The secure storage may eliminate the stored data, for example, after the configured amount of time. The secure storage may perform an automatic deletion of the data. The automatic deletion may be associated with conditions. The automatic deletion may be modified (e.g., the amount of time before deletion may be extended/shorted and/or the automatic deletion may be cancelled) based on the conditions. The conditions may be associated with events, for example, that may occur after storage, such as, patient complications, readmission, hospital acquired infections, legal/billing issues, and/or the like.

Figure 10:
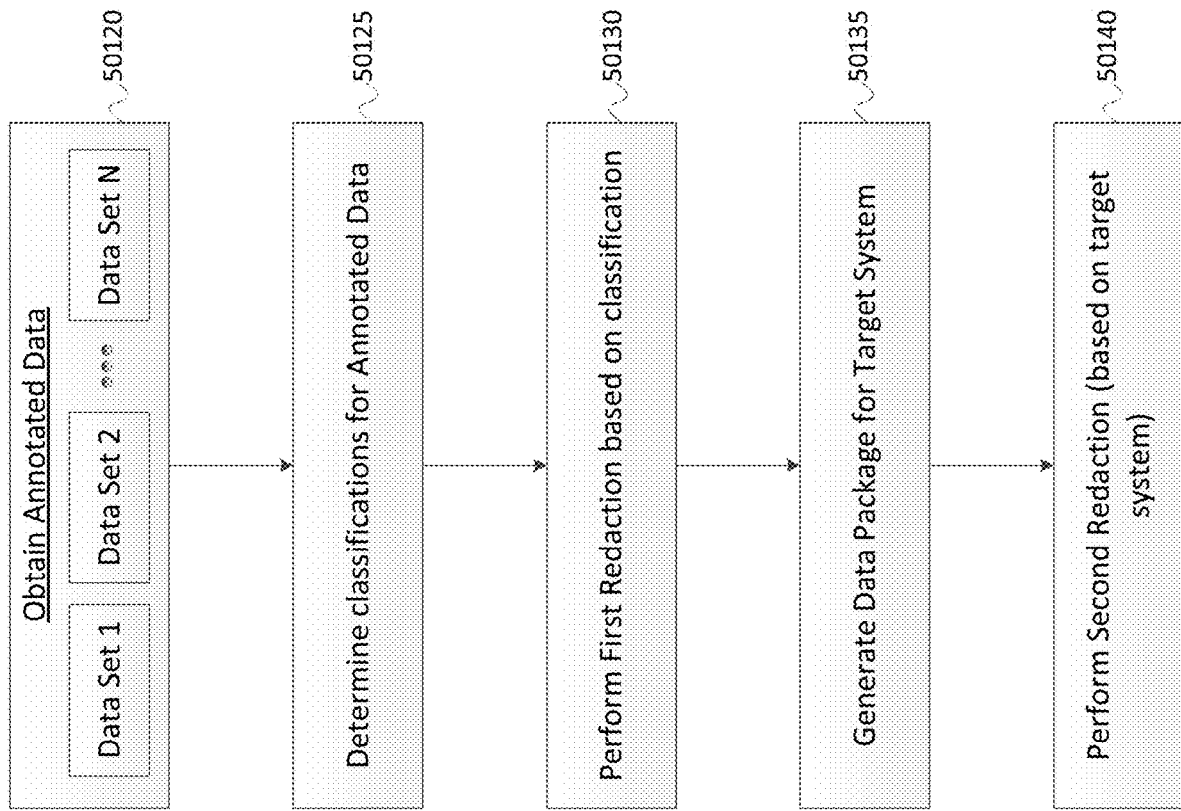
FIG. 10 illustrates an example of selectively redacting of data in a data set.

FIG. 10 illustrates an example of selectively redacting of data in a data set. As shown at 50120, surgical procedure data (e.g., annotated surgical procedure data) may be obtained. The surgical procedure data may include multiple dataset(s). At 50125, a classification may be determined for the surgical procedure data. The surgical procedure data, dataset(s) within the surgical procedure data, portions of surgical procedure data, subsets of surgical procedure data, etc. may be associated with a classification.

For example, a subset of the surgical data may be classified as confidential information (e.g., in terms of HIPAA). For example, a subset of surgical data may be classified as inaccurate, erroneous, an outlier, and/or the like.

At 50130, a first redaction may be performed on the surgical procedure data, for example, based on the determined classification. Confidential information may be redacted, for example, before sending to a different system (e.g., target device). The subset of the surgical data may be redacted (e.g., required to be redacted) before sending the data, for example, based on the classification of being confidential information (e.g., in terms of HIPAA). The subset of the surgical data may be redated, for example, based on the subset of surgical data being classified as inaccurate. The computing system may determine to refrain from redacting the inaccurate surgical data, for example, to notify HCPs about the inaccurate data. For example, if the HCP is aware of the inaccurate data, the HCP may alter surgical procedure steps or use different surgical equipment.

At 50135, the data package(s) for the associated target system(s) may be generated. The data package(s) may include the redacted data.

At 50140, a second redaction may be performed, for example, on at least a portion of the data in the data packages. For example, the second redaction may be performed based on the target system associated with the data package. For example, the target system may be outside HIPAA boundaries and subject to confidentiality rules. Confidential information (e.g., in terms of HIPAA) may be redacted before sending the data to the target system outside HIPAA boundaries. A target system may within HIPAA boundaries, where the same confidential information may not be redacted (e.g., may not be required to be redacted).

Surgical procedure data determined to be redacted may be stored, for example, before performing the redaction. For example, surgical procedure data determined to be confidential information (e.g., with respect to HIPAA) may be redacted before being sent outside the HIPAA boundary. The surgical computing system may store the surgical procedure data to be redacted in a local storage, for example, to preserve the surgical procedure data. The surgical procedure data to be redacted may be stored, for example, as a backup and/or if the surgical procedure data to be redacted is needed at a later time.

Automated data packages may be generated for facility systems. The automated data packages may be sent to facility systems, for example, to schedule device/tool replacement, repair and/or cleanup of an operating room, replenishing consumables in a facility room, and/or the like.

For example, a data package may be sent to a facility product re-ordering system. The data package may include data associated with products used in a surgical procedure. The data associated with the products used during the surgical procedure may indicate the consumable resources that were used in a previous surgical procedure and are missing in the operating room for a planned surgical procedure. The data package may indicate that the product to be replenished is not in stock in the facility, for example, based on facility information. The data package may indicate a request to the facility product re-ordering system to indicate when the earliest the planned surgical procedure can be conducted (e.g., because of the delay in restocking the missing consumable) and/or indicate alternative instruments/consumables that may be used to conduct the planned surgical procedure (e.g., to make the procedure occur earlier).

A data package may be sent to a facility system associated with cleaning and maintenance. For example, the data package may include data associated with the planned surgical procedure, the tools/devices/equipment used in the planned surgical procedure, the tools/devices/equipment currently stocked in the operating room, and/or the like. The data package may include data verifying that the surgical tools/devices/equipment are present and ready for use for the planned surgical procedure. The data package may include data indicating that the operating room is not ready for the planned surgical procedure and/or indicate a time that the operating room will be ready.

A data package may be sent to a facility system associated with sterilization (e.g., of surgical equipment and/or tools in an operating room). For example, the data package may include data that indicates verification of the instruments/devices/equipment that will be used in the planned surgical procedure. The data package may include data that indicates that surgical equipment for the planned surgical procedure is sterile and/or ready to use for the planned surgical procedure. The data package may include data that indicates that the surgical equipment is not cleaned. The data package may include data that indicates that the surgical equipment is in the process of being cleaned. The data package may include data that indicates a prioritization of a specific surgical device/tool/equipment for sterilization (e.g., that is currently not clean or is unavailable).

A data package may be sent to a facility system associated with staffing and surgical procedure timing. For example, the data package may include data indicating the planned surgical procedure timing. The data package may include data associated with the HCPs scheduled for the surgical procedure. The data package may include identification information associated with the staff. For example, specific surgical tasks may be performed by specific HCP roles in the surgical procedure. The data package may indicate staff that are suitable for the surgical task. The data packages may indicate staff that are available for the surgical procedure. The data packages may indicate staff based on a classification, such as surgeon preference, OR setup, and/or the like.

The data package(s) may be sent to the target system(s), for example, for surgical procedure documentation. The data package(s) may be sent for automated population of the surgical procedure documentation. The data package(s) may be sent to system databases (e.g., linked system databases in the facility). The data package(s) may be associated with updating, annotating, and/or transcribing information associated with the surgical procedure.

The data package(s) may be sent to the target system(s), for example, for billing population, annotation, and/or classification. The data package(s) may include information associated with surgical procedure steps performed in the surgical procedure. The information associated with the surgical procedure steps performed in the surgical procedure may be linked to billing codes (e.g., diagnosis related group billing codes). The data package(s) may include data used by the facility billing systems to track the billing information.

For example, the computing system may determine the data to include in the data package for the billing systems. The computing system may further annotate the data in the data package (e.g., tag with metadata), for example, to classify the data with associated billing codes. The annotated data may be used to update the data sets to be used by the target system(s). The data package(s) may be sent to the target system(s), for example, for billing tasks.

The data package(s) may be sent to the target system(s), for example, for stock maintenance (e.g., consumable maintenance, surgical tool maintenance, surgical device maintenance, and/or the like). For example, the data package(s) may include information indicating products used (e.g., pulled) during the surgical procedure. The data package(s) may include information indicating the serial number associated with the products used. The data package(s) may include information indicating the number of uses for a surgical tool, surgical device, and/or surgical equipment during the surgical procedure. The data package(s) may include information indicating that the surgical tool, surgical device, and/or surgical equipment are due for maintenance, replacement, repair, disposal, returning, sterilization, cleaning, and/or the like. The data package(s) may include information indicating any issues and/or notes associated with the product use during the surgical procedure (e.g., if there were issues using the product and/or the product malfunctioned).

The data package(s) may be sent to the target system(s), for example, for electronic medical record (EMR) database population. For example, the data package(s) may include information associated with the patient and the surgical procedure. The data package(s) may include information associated with the details, annotations, recordings, procedure notes, and/or the like from the surgical procedure. The data package(s) may be used to update (e.g., automatically update) the EMR database for the patient's record. The data package(s) may include information associated with the surgical procedure aspect, surgical instruments used, surgical tasks performed, alternative treatments that were performed, and/or the like. The data package(s) may include the surgical video(s) (e.g., annotated surgical video(s)) associated with the surgical procedure. The surgical video(s) may be used as a record of the surgical procedure and a record for the surgical steps and/or surgical tasks conducted during the surgical procedure.

The dissemination of information/data (e.g., automated dissemination of information/data) may be documented/annotated. For example, the automated steps performed associated with one or more of obtaining surgical procedure data, annotating surgical procedure data, determining the target system(s), determining the data needs associated with the target system(s), generating the data packages for the target system(s), redaction of a portion of the data, sending the data package to the target system(s), etc. may be documented (e.g., annotated). For example, the computing system may document and/or record the autonomous operation associated with the dissemination of the surgical procedure data. The surgical computing system may document and/or record user responses to the autonomous operation (e.g., overrides, verifications, confirmations, and/or the like).

The computing system (e.g., if performing automated dissemination of data to target systems) may document responses to the data sets and actions taken with respect to the data sets. Machine learning data may be generated, for example, based on the computing system's responses to datasets. The machine learning data may be used to train an artificial intelligence (AI) model. The AI model may be trained and/or used for performing subsequent automation tasks. The machine learning data may be associated with one or more of the following: a failure of a surgical device/tool, degraded performance (e.g., associated with a surgical device/tool, user technique actions, and/or the like), data relating to user biomarkers, surgical procedure steps, staff interactions, user behavior (e.g., related to an unexpected event), and/or the like.

The computing system may generate machine learning data associated with a failure of a surgical device during a surgical procedure. For example, the computing system may determine that a surgical device failed to perform properly and/or generated inaccurate data. The computing system may determine the surgical device failure, for example, based on other surgical procedure data obtained during the surgical procedure. The computing system may determine to adjust the magnitude of inaccurate data associated with a surgical device, for example, based on the other surgical procedure data obtained during the surgical procedure. The computing system may generate machine data associated with the recalibration (e.g., adjusting the magnitude of the inaccurate data). The computing system may determine a type of failure associated with the surgical device. The type of failure may be used, for example, to escalate the magnitude of associated data (e.g., surrounding data generated by associated devices) that may be attached to the failure data. The machine learning data may indicate devices associated with the surgical device failure (e.g., that provide to and/or use data associated with the surgical device failure). The machine learning data may indicate that the associated devices may need to be augmented (e.g., adjusted) and/or recorded, for example to limit (e.g., minimize) the propagation of failure and/or improve device to device reliance.

The computing system may generate machine learning data associated with degraded performance, for example, associated with user technique actions, surgical instruments, and/or the like. For example, machine learning data may be generated that indicates that performance has fallen below a threshold. The performance may have degraded, for example, based on the user technique actions and/or surgical instrument. The machine learning data may be generated based on tracking of the user control interaction coupled with a surgical instrument. The machine learning data may include recorded data indicating a repeated user-controlled action, for example, that may result in degraded function. The machine learning data may be applied to an AI model, for example, to prevent performing the user-controlled action coupled with the surgical instrument that resulted in degraded function. The AI model may improve to prevent subsequent surgical procedures from using the operations that are associated with degraded performance and/or function.

The computing system may generate machine learning data associated with improved performance (e.g., unexpected improved performance). For example, the computing system may determine that user techniques associated with a surgical instrument is performing above a threshold. The computing system may record/document surgical procedure data (e.g., from the surgical hub), for example, to investigate the performance (e.g., to determine the cause of the improved performance). The recorded surgical procedure data may include information associated with the events occurring in the OR during the surgical procedure during the improved performance. The computing system may obtain diagnostic data (e.g., request device diagnostic data) for systems (e.g., internal systems), for example, to determine whether the systems (e.g., internal systems) have been affected. The computing system may enable the surgical hub to request associated devices (e.g., devices associated with the improved performance) to perform internal diagnostic checks. The machine learning data associated with the improved performance may include an indication that indicates (e.g., to a user) to provide additional information (e.g., contextual information) on tasks/techniques that may have been performed differently (e.g., which may have caused the improved performance). The computing system may determine (e.g., verify) whether the system associated with the improved performance actually experienced an improved performance. For example, the computing system may indicate (e.g., to a user) to verify that the result was unanticipated. The computing system may verify that the algorithm associated with determined whether there is improved performance is accurately rating performance.

The computing system may generate machine learning data associated with metadata relating to use biomarkers, procedure steps, staff interactions, user behavior, and/or other surgical events/interactions (e.g., related to an unexpected event). For example, the machine learning data may include documentation of medicines and/or patient biomarkers that may be associated with the unexpected event. The machine learning data may include staffing information, for example, such as the presence of staff in the OR at the time of the unexpected event. The machine learning data may include the surgical procedure step and/or sequential action variances to the surgical procedure plan. For example, variances to the surgical procedure plan may include deviations of action from the initial procedure plan, such as, changes of approach to a surgical site (e.g., internally and/or trocar placement), that may have contributed to the unexpected event. Variances to the surgical procedure plan may include unanticipated complications (e.g., excessive adhesions encountered during mobilization). The machine learning data may include biomarkers of the staff, for example, that may indicate that the biomarkers are elevated and/or depressed irregularly from a steady state (e.g., a threshold state). The machine learning data may include a listing of available surgical instruments that the user chose not to use.

For example, the computing system may document (e.g., perform automated documentation) user responses, which may include creating data associated with a user's reaction to the computing system's performed operations (e.g., autonomous operations, such as annotating datasets and/or generating data packages for target systems using the annotated datasets). For example, the computing system may determine that a user performed an override action on an autonomous operation (e.g., operation associated with selective dissemination of data/information to the target system(s)). The computing system may create machine learning data associated with the override action, for example, such that the AI model learns that the performed autonomous action is associated with an override action by the user. The machine learning data may include data associated with the events and/or the risk of events leading up to the user override. The AI model may be used to perform subsequent autonomous actions. The computing system may use the AI model to avoid performing the autonomous action associated with the override action.

The computing system may determine retention conditions for surgical procedure data. For example, the computing system may determine to keep data in storage for longer/shorter periods based on one or more of the following: storage space availability, communication ability, system utilization, level of the data, facility rules, retention procedures, and/or the like. For example, data retention for data may be determined based on the storage space or communication constriction (e.g., low storage space). For example, data may be retained for a shorter amount of time based on the storage space and/or communication constriction. Less data may be stored based on the storage space and/or communication constriction (e.g., as compared with data storage if the storage space is not limited and/or communication is not constricted). The computing system may indicate to scale down storage and/or retention, for example, based on successful results and/or lack of events. Storage overload may trigger alternative operations for storage and/or archival of data.

A hierarchy of data retention may be used. For example, a level of data may be adjusted based on a retention period. Metadata may be released and deleted at a differing retention period. A hierarchy of data retention may be determined, for example, based on a depth, measure, and/or relationship to the patient. For example, patient biomarker data may be associated with the longest retention. The patient biomarker may be input to electronic medical records (e.g., for long retention). Annotated video data may have a longer retention period than secondary instrument data. The source and/or integrity of the data may affect the data retention. For example, calculated and/or derived data may be associated with a shorter retention period than directly measured data. Video and/or timeline-based data may be associated with a long retention period as compared to annotations and/or overlaid data on the video. Product inquiry data may be associated with different levels of data retention. For example, product inquiry may have a different retention period than other instrument operation parameters. A user request may be used to adjust the product inquiry retention period of data. In examples, patient recovery events may be used to release data from storage.

The computing system may generate machine learning data associated with the outcomes resulting from automated operations. For example, the machine learning data may include data associated with expected outcomes and actual outcomes associated with the planned automated operations. The machine learning data may flag operations involving automation. The machine learning data may flag successful performance of an automated operation, for example, relative to the expected outcome (e.g., planned response). The machine learning data may flag automated operations that were modified and/or overridden. The machine learning data may include characterizations associated with the automated steps, for example, to enable user oversight and improved trust that the automated operation was successful (e.g., completed the task successfully.

For example, automated operations may be associated with a pre-procedure CT scan, an MRI, and/or an active lap imaging. The scans and/or imaging may be used in an automated operation, for example, to identify and/or highlight the margins of the tumor (e.g., based on linking together landmarks and linking points). The user may see the real-time imaging from the scans and/or images. The user may determine the margins based on the real-time imagine. The user may determine that the margins (e.g., margins generated by the automated operation and/or margins determined by the user) need to be adjusted based on the automated operation. Verification that the margin creation steps were performed accurately may be performed. Identification of additional information determined at real-time (e.g., that caused an adjustment to the margins) may be performed.

Storage of surgical procedure data may be automated. The target systems (e.g., the computing system may send data packages to) may be storage systems. For example, the storage systems may be automatically determined. The location and/or duration of surgical procedure data storage may be determined (e.g., automatically determined). Recall parameters associated with the store surgical procedure data may be determined. Recall parameters may be associated with how the stored surgical procedure data may be recalled, when the stored surgical procedure data may be recalled, and/or how the surgical procedure data may be recalled. For example, the stored surgical procedure data may be recalled based on monitored data (e.g., current surgical procedure data).

Storage identification and/or pruning may be automated. For example, identification and/or segmentation of the data for transport (e.g., data packages) may be automated. The data packages may be generated (e.g., as described herein) and sent to the target system(s) that may use (e.g., require) the information in the data packages. The computing system may determine a retention period associated with the sent data package, an archival method for the data package, and/or a storage location for the data package. The computing system may determine redaction and/or a protected configuration of the data within the data package, for example, for the target system the data package is sent to. The data package may include segregated data. The data in the data package may be segregated based on a surgical job/task, an outcome, a constraint, a technique, a user, a procedural step, and/or the like. The data package may be organized based on the segregations in the data package. For example, data for linked and/or similar procedure steps may be segmented (e.g., for review and/or export). For example, data associated with a particular surgical instrument (e.g., an Enseal device) may be pooled together for review together, which may allow the users, facility, and/or manufacturer to review the operation together. A storage location may be determined for erroneous and/or irregular surgical procedure data. The computing system may use an alternative process for storage and/or review of the data, for example, if the data is determined to be erroneous and/or irregular. Data resulting in an incident and/or complication may be stored differently.

Surgical procedures may use patient specific procedure plans in planning and executing a surgery. Creating a patient-specific procedure plan for an operation may be performed manually by healthcare professionals and takes a lot of time and effort. Healthcare professionals may parse through large amounts of pre-surgical data and patient specific data in planning surgeries for a patient. The time spent devising the patient specific procedure plan may include time spent not performing other duties. However, surgeons cannot just use a procedure plan template for each surgery as each surgery is tailored to a patient's specific needs. There are many variables to take into account when determining a patient specific procedure plan.

Figure 11:
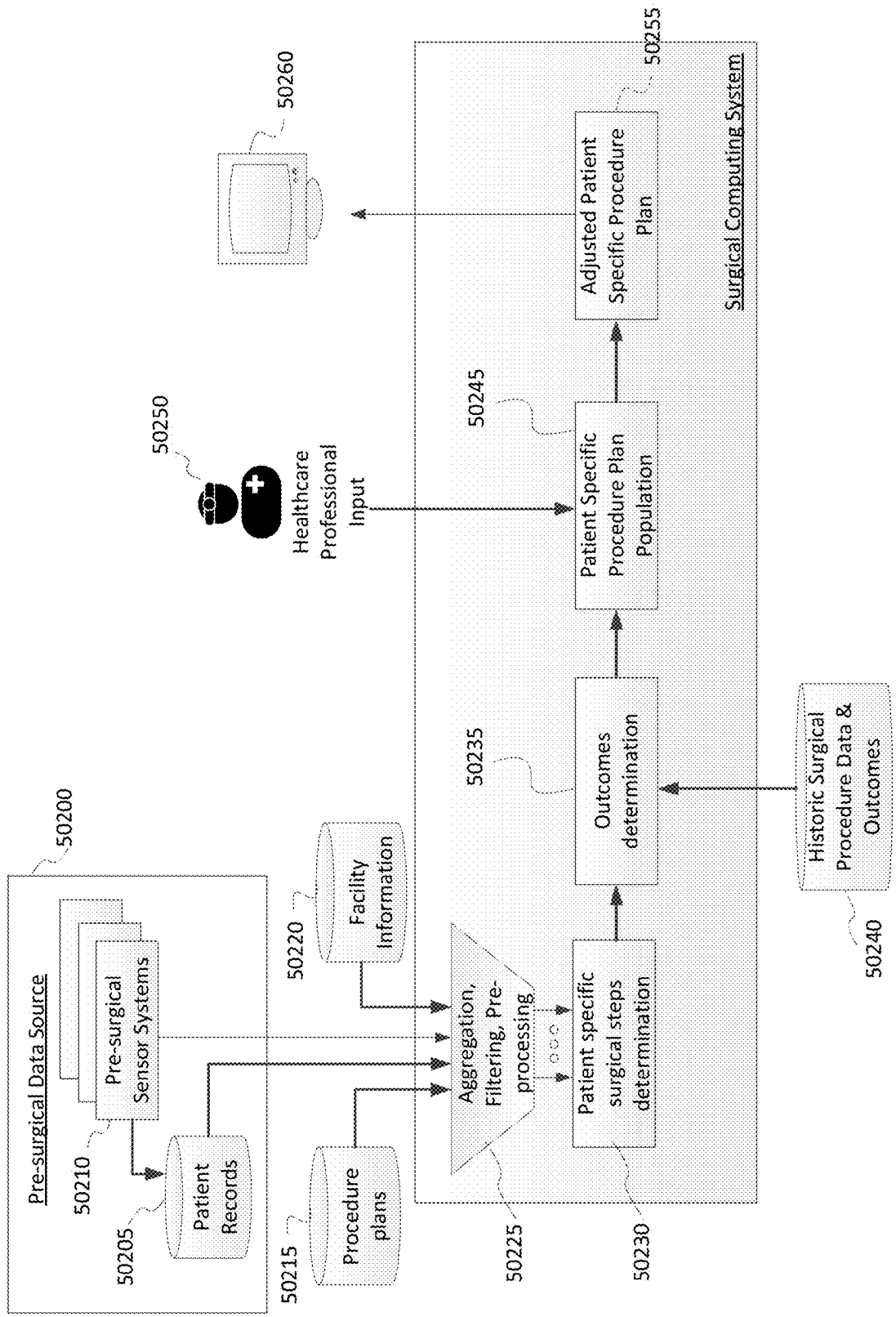
FIG. 11 illustrates an example aggregation of pre-surgical data and generation of a patient specific procedure plan.

FIG. 11 illustrates an example aggregation of pre-surgical data and generation of a patient specific procedure plan. As shown in FIG. 11, a surgical computing system may obtain surgical procedure data (e.g., pre-surgical procedure data). The surgical procedure data may be used to generate a patient specific procedure plan. The surgical procedure data may be associated with pre-surgical data sources 50200 (e.g., scans, images, electronic medical records, etc.), procedure plans 50215 (e.g., procedure plan templates), facility information 50220 (e.g., staffing, room availabilities, etc.), and/or the like. The pre-surgical data sources may include patient records 50205 and/or pre-surgical sensor systems 50210. The surgical procedure data may be patient-specific surgical procedure data. Patient-specific surgical procedure data may include data associated with a patient and/or a patient's scheduled surgical procedure. For example, patient-specific surgical procedure data may include pre-surgical tests and/or images obtained for a planned surgical procedure.

The surgical procedure data may be automatically collected. For example, the surgical computing system may automatically obtain surgical procedure data associated with a patient specific surgical procedure. The surgical computing system may send requests for and may receive information associated with the patient and/or patient specific surgical procedure. Scans, images, and/or tests (e.g., preoperative scans, images and/or tests) performed may be automatically collected for the surgical procedure. Surgical procedure data may be collected from patient biomarker systems, patient records, and/or other pre-surgical sensor systems.

As shown at 50225 in FIG. 11, the surgical procedure data may be processed. For example, the surgical procedure data may be aggregated and/or compiled. The surgical procedure data may be synchronized, for example, during the aggregation. The aggregation may include summarizing the surgical procedure data. The aggregation may include alignment of the surgical procedure data, for example, such as aligning preoperative images. For example, the surgical procedure data may include different presurgical patient images. The aggregation may include aligning the pre-surgical patient images and/or overlaying the images, for example, to provide context for the patient specific surgical procedure. The aligned pre-surgical patient images may be used to identify areas for the surgical procedure (e.g., tumors, surgical sites, organs, etc.) and/or blind spots in the images.

The surgical procedure data may be filtered. Filtering may be performed to determine inaccurate and/or missing surgical procedure data. Filtering may be performed, for example, so the surgical procedure data may be interpreted. Pre-processing may be performed on the surgical data, for example, to condition the data for analysis.

For example, the surgical procedure data may be processed for aggregation and/or compiling into a baseline procedure plan starting point. Surgical procedure data may be used to determine subsurface and/or volumetric information associated with a patient's anatomy. For example, medical imaging (e.g., X-ray, fluoroscopy, MRI, CT, and/or ultrasound scans) may provide information associated with the patient's anatomy. The surgical procedure data may be used (e.g., multiple images may be used and/or aggregated) to plan and/or intraoperatively guide a surgical procedure. Target surgical sites and/or supplementary landmarks may be identified, for example, using the surgical procedure data. The surgical procedure data may be used in automation of image processing and/or pattern recognition algorithms, for example, to determine a location associated with features (e.g., unique features) that may be used as a reference point in the surgical procedure. Image sources (e.g., multiple image sources) may enable an artificial intelligence system to process images (e.g., instantly) and/or make decisions based on the target sites and landmarks in navigating to the site. Image sources may enable spatial awareness, for example, for a guidance system. The surgical procedure data (e.g., preoperative images) may register with the patient on the operating table, for example, so the system may identify a path (e.g., optimal path) for the surgeon to follow and/or continue autonomously. The computing system may identify insertion points (e.g., alternative insertion points) and/or indicate the insertion points to the surgeon, for example, for additional instruments and/or trocar placement. Medical images may be used as feedback (e.g., real-time feedback) for a surgical procedure. The medical images used as feedback may improve surgical precision, improve accuracy, reduce margins, avoid sensitive tissues and nerves, improve consistency of treatments, and/or the like. Fiducial markers (e.g., additional fiducial markers) may be implanted (e.g., which may create landmark during the imaging, for example, for the processing of the image(s) and/or use of reregistering when the patient was on the operating table.

Patient pre-surgical data may be aggregated. Aggregated pre-surgical data may include the patient's biometrics, medical records, diagnostic imaging, disease state and/or progression, previous treatments, and/or the like. The aggregated pre-surgical data may be used to create a baseline procedure plan. The baseline procedure plan may include variables for the surgical procedure, such as, for example, access, patient positioning, preferred instrument mix, and/or the like. The surgeon may simulate the created baseline procedure plan, adjust the plan, add to the plan, and/or modify variables in the plan.

Relationships and/or interactions between data in the patient pre-surgical data may be identified. For example, data in the patient pre-surgical data may be conflicting. Data in the patient-pre-surgical data may be related and/or amplify each other. For example, interactive biomarkers may be highlighted (e.g., automatically highlighted) based on a determination that the biomarkers are related.

Thresholds of combined and/or interrelated effects of the patient pre-surgical data may be indicated. For example, patient pre-surgical data may interrelate above a threshold amount, which may affect how the pre-surgical data should be analyzed. For example, a patient may be taking a blood thinner (e.g., Warfrin and/or Heparin) to minimize blood clot complications. A blood test may indicate low platelet counts. A relationship (e.g., interaction) between the blood thinner and the low platelet count may be determined. The cumulative impact of bleeding may be greater than what the dosage of the blood thinner would account for. A higher probability of bleeding in the surgical procedure may be determined and indicated (e.g., in the baseline procedure plan). The surgeon may determine to modify the baseline procedure plan, for example, based on the indication of the increased bleeding risk. In an example, the computing system may modify the baseline procedure plan, for example, based on the determination of the increased bleeding risk. An alternative surgical step (e.g., different energy device, different surgical approach, different mobilization path for freeing up resected tissue, and/or use secondary hemostat adjunct), for example, may be used to account for the co-morbidity interaction.

Biomarkers, treatments, and/or pre-operative steps (e.g., pre-operative targets) may be determined to be conflicting and/or beyond a threshold within a baseline procedure plan. The conflicting biomarkers, treatments, and/or pre-operative steps may be identified. The conflicts may be highlighted, for example, in the baseline procedure plan. For example, heart rate and/or blood pressure biomarkers may be high in the pre-operative assessment or monitoring. The patient may be taking medication for the heart rate and/or blood pressure. A conflict may be determined based on that the biomarkers should be in lower range based on the use of the drug. The discrepancy (e.g., irregularity) may be highlighted and/or indicated to the surgeon. The surgeon may use the discrepancy to determine a course of action (e.g., treatment plan and/or modification to the baseline procedure plan).

Images (e.g., pre-operative images) and/or tests (e.g., pre-operative tests) may be summarized, aggregated, and/or aligned (e.g., automatically aligned). The summary, aggregation, and/or alignment may be included in the baseline procedure plan. Proposed adaptions for a baseline procedure plan, for example, may be determined based on the pre-operative data. For example, pre-operative scans may be imported and/or overlaid onto the baseline procedure plan. The overlay may indicate tumor location. The tumor location may be aligned between the scans, which may allow the user (e.g., surgeon) to visualize the location and/or orientation of the tumor. Different angles from different images may provide a better context for tumor location. The overlaid images may be used to adjust baseline margins to align with the tumor scan integrations.

Overlaid images may be used to indicate blind spots and/or lack of visualization. Blind spots may lead to an issue during the surgical procedure. The indication of blinds spots and/or lack of visualization may indicate that data is questionable and/or absent. If data is questionable and/or absent, alternative surgical tasks and/or methods may be determined. Other data may be substituted in for the questionable and/or absent data, for example, from a different imaging source (e.g., live imaging source) and/or a different pre-operative scan.

Figure 12:
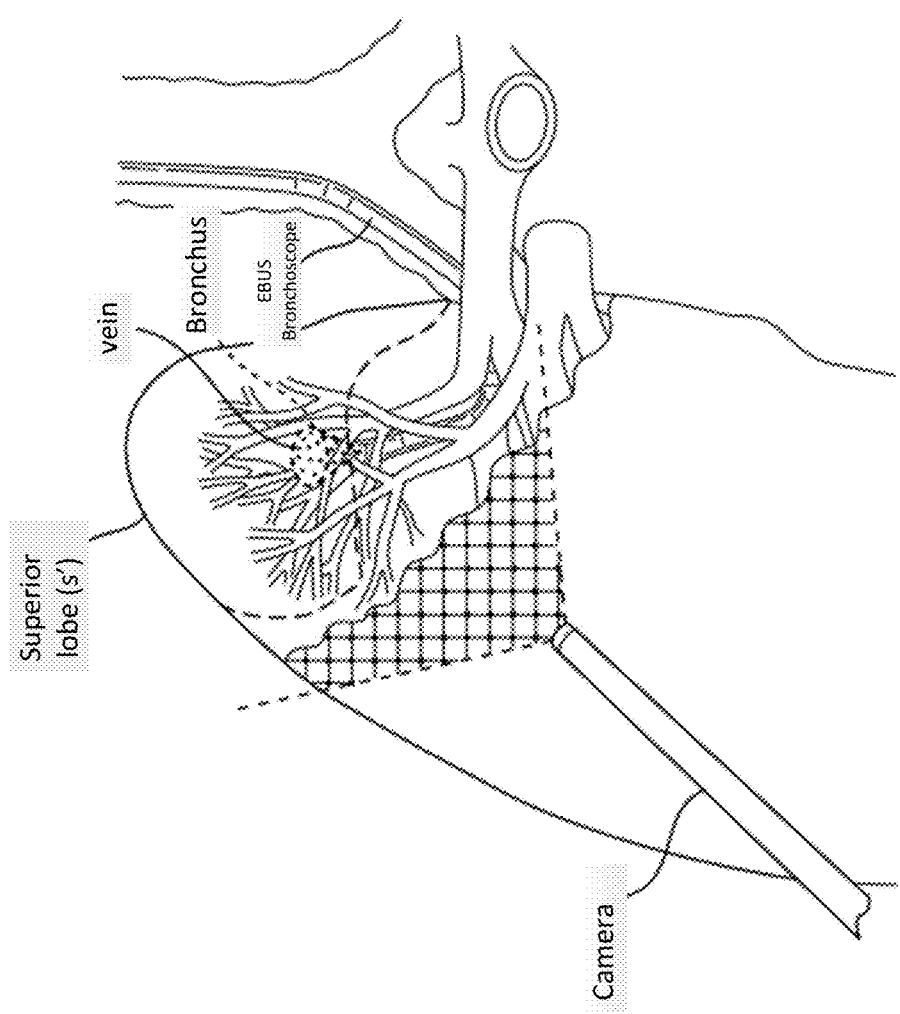
FIG. 12 illustrates an example of an image of a lung generated from multiple sources.
Figure 13:
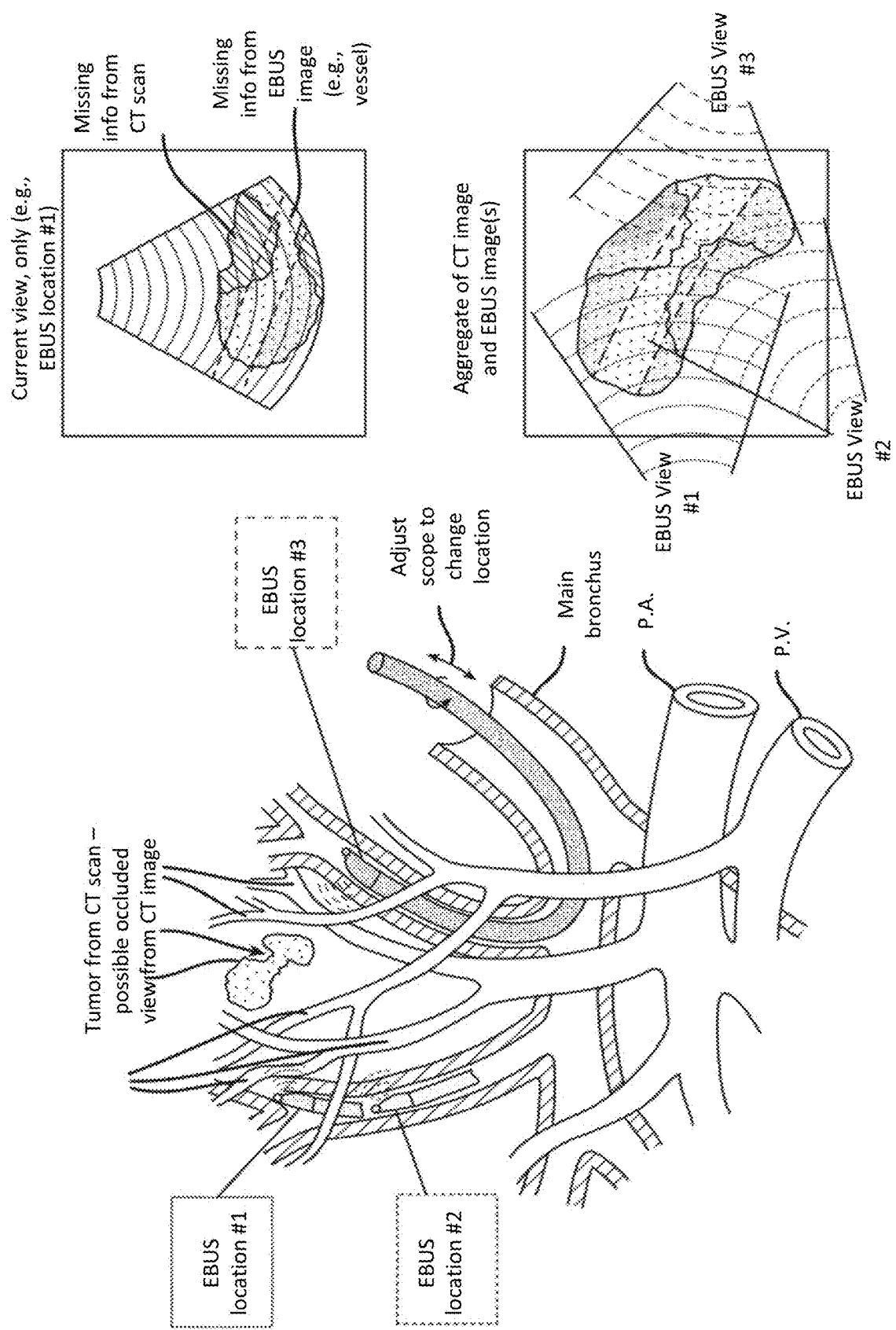
FIG. 13 illustrates an example image sourced by a laparoscopic camera or endobronchial ultrasound bronchoscopy (EBUS) to fill in missing portions of a full 3D view.

FIG. 12 illustrates an example of an image of a lung generated from multiple sources. A computerize tomography (CT) scan of a lung may be obtained. In examples, portions of an image may be occluded from the CT view of the tumor. The tumor may be occluded, for example, in a CT scan. FIG. 13 illustrates an example image sourced by a laparoscopic camera or endobronchial ultrasound bronchoscopy (EBUS) to fill in missing portions of a full 3D view. As shown in FIG. 13, a laparoscopic camera or EBUS may be used to fill in visualizations missing from other scans. The scans may be aggregated to get a full picture of the lungs. Each scan may not be able to produce a complete image, but aggregating the images may provide a clearer picture to fill in missing portions. Different cameras and/or camera angles may be used to provide the complete lung image. The aggregated image may be provided to the user to convey necessary information. The aggregated image may indicate that information may be needed to be input to complete any missing information and/or indicate that the scans may need to be reperformed. The information missing from the occluded view from the CT scan may be supplemented by aggregating different images from different sources, for example, to provide a complete picture.

Patient-specific surgical steps may be determined, for example, as shown at 50230. The patient-specific surgical procedure may include patient-specific surgical steps. The patient-specific surgical steps may be determined based on the surgical procedure data (e.g., processed surgical procedure data). For example, the patient specific-surgical steps may be determined based on the pre-surgical data sources and a procedure plan template associated with a planned surgical procedure. For example, a thoracic surgical procedure may be planned for a patient. The patient specific surgical procedure may use a thoracic surgical procedure plan template to plan the procedure. The pre-surgical data sources (e.g., with the thoracic surgical procedure plan template) may be used to determine the patient-specific surgical procedure steps.

The patient-specific surgical steps may be associated with surgical tasks. Surgical procedures may be performed using one or more alternative surgical tasks. Surgical tasks may be performed using one or more alternative surgical instruments. For example, a surgical task may involve using a surgical stapler. The surgical task may be completed by the surgical stapler using one or more energy levels, such as, for example, a first energy level or a second energy level. Using the first energy level with the surgical stapler may lead to a first outcome and using the second energy level with the surgical stapler may lead to a second outcome. The first outcome may be improved over the second outcome. The surgical task and/or surgical steps associated with the better outcomes (e.g., as compared with alternative tasks and/or steps) may be preferred for a surgical procedure. Performing a surgical task in a surgical procedure step may affect subsequent surgical tasks and/or subsequent surgical procedure steps. For example, performing a surgical task may affect the rest of the surgical tasks to be performed during the surgical procedure.

The patient specific surgical tasks may be associated with better outcomes, for example, as compared with generic surgical tasks in a surgical procedure plan template. Accommodating a patient's needs and/or the facility's resources may enable a more efficient and/or successful outcome for the surgical procedure. The patient specific surgical tasks may be determined, for example, based on patient specific information, the facility information, staffing information (e.g., HCP availabilities, HCP roles, HCP experience, HCP specialties, etc.), and/or the like.

Characterizations may be determined for the patient specific surgical steps. The patient specific surgical steps may be characterized, for example, based on outcome success, efficiency, risk, efficacy, and/or the like. For example, a patient specific surgical step may be associated with a range associated with outcome success. Patient specific surgical steps may be associated with different surgical outcomes. Characterizations may be determined, for example, based on the patient-specific surgical data and/or historic data associated with the surgical procedure.

In examples, an outcome success for a surgical task option may be characterized. Based on the patient-specific surgical data, an outcome success for a surgical task option may be determined. For example, a first surgical task option may involve using a surgical stapler with a first set of parameters and a second surgical task option may involve using a surgical stapler with a second set of parameters. The first set of parameters and the second set of parameters may result in different outcomes based on the patient's anatomy and/or patient-specific surgical data. For example, if a patient is prone to bleeding, a set of parameters that may increase bleeding may be associated with a lower outcome success. The outcome successes may be characterized, for example, to help select which surgical task option to use in the surgical procedure.

In examples, risk for a surgical task option may be characterized. Based on the patient-specific surgical data, a risk level (e.g., critical risk, moderate risk, low risk, no risk, etc.) may be determined for a surgical task option. For example, a first surgical task option using a first surgical device may create more risk for a patient as compared to a second surgical task option using a second surgical device. The first surgical task option may create more risk, for example, because the first surgical device may negatively interact with the patient based on the patient's anatomy and/or patient-specific surgical data. The first surgical task option may pose a critical risk for the patient, whereas the second surgical task option may pose a moderate risk. The characterized risk levels may be used, for example, to select a surgical task option to use in the surgical procedure.

In examples, efficiency for a surgical task option may be characterized. Based on the patient-specific surgical data, efficiency associated with performing a surgical task may be determined. A first surgical task option may be completed more efficiently than a second surgical task option, for example, based on the surgical device used. For example, a surgical device with a stronger energy generation may hasten the surgical procedure, as compared to a surgical device with a weaker energy generation. Efficiency of a surgical task option may be affected by patient anatomy and/or patient-specific surgical data. For example, a patient's anatomy may lend itself to a certain surgical device over another, which may increase the efficiency of the surgical task option.

Outcomes may be determined (e.g., predicted) for surgical tasks and/or surgical procedure steps, for example, as shown at 50235. Outcomes may be associated with surgical outcomes, complications, efficiency, and/or the like. Outcomes may be determined, for example, based on patient risk, patient survivability, procedure time, and/or the like (e.g., which may be determined based on the obtained data). For example, a first outcome may be determined (e.g., predicted) for a first (e.g., primary) surgical task and a second outcome may be determined (e.g., predicted) for a second (e.g., alternative) surgical task. The first outcome may be associated with a higher success rate as compared with the second outcome. The first outcome may have a higher success rate, for example, based on the patient specific data. For example, if the first surgical task uses a first surgical tool and the second surgical task uses a second surgical tool, the first surgical tool may be more appropriate given the surgical procedure and/or the patient. Therefore, using the first surgical tool may result in a better chance of success.

Outcomes may be determined for surgical tasks, for example, even when there is incomplete and/or conflicting data (e.g., that is used to determine the outcome). For example, data may be conflicting and/or incomplete which may lead to an incorrect outcome prediction. The outcome prediction may take into account the conflicting and/or incomplete data, for example, when determining the outcome. An indication may be sent, for example, that may indicate that the determined outcome is determined based on incomplete and/or conflicting information. The indication may indicate an outcome prediction certainty associated with a typical procedure (e.g., without missing information). The indication may indicate that the determined outcome may be refined, for example, by verifying and/or providing the correct information (e.g., used in the outcome determination). For example, an outcome may be determined for a first surgical task. The outcome may be determined based on incomplete information. The outcome may indicate an outcome prediction certainty range (e.g., 70-90%). The outcome may indicate to the HCP to provide information to refine the outcome prediction certainty range. An HCP may provide the missing information. Using the provided missing information, the outcome prediction certainty range may be refined (e.g., to be 85%-90%).

Outcomes may be determined based on previous surgical procedure data (e.g., from previous procedures) and/or previous surgical procedure outcomes. As shown at 50240, historic surgical procedure data and/or outcomes may be obtained (e.g., from a cloud storage). The historic surgical procedure data and/or outcomes may be used to determine outcomes associated with a current surgical procedure and/or surgical task. The predicted outcome may be stored in the historic procedure data and/or outcomes. The actual outcome of the surgical task/step/procedure may be stored in the historic surgical procedure data and/or outcomes, for example, after the surgical task/step/procedure is collected. The historic data may be used to calculate outcome predictions in subsequent surgical procedures.

The historic surgical procedure data and/or outcomes may be used, for example, to provide context to the patient specific surgical steps/tasks. For example, a cloud aggregation of the outcomes from historic results may be used to provide context associated with the patient specific surgical steps/tasks (e.g., highlight the implication on the patient specific surgical tasks/steps and/or baseline plan). The historic surgical procedure data and/or outcomes may be used to adapt the patient specific surgical steps/tasks (e.g., the baseline procedure plan), for example, based on changes in practices (e.g., best practices), clinical trends, and/or the like. The historic surgical procedure data and/or outcomes may be overlaid on the patient specific surgical step/task and/or modified by the patient data, for example, to identify surgical decision points (e.g., for the user to consider in planning the surgical procedure).

A patient specific procedure plan may be populated, for example, as shown at 50245. The patient specific procedure plan may be populated with surgical steps and/or patient specific surgical tasks. The surgical tasks may be the surgical tasks determined based on the patient specific presurgical data (e.g., attributed with a predicted outcome). The patient specific procedure plan may include a recommended set of surgical steps/tasks (e.g., for each surgical procedure step/task). The patient specific procedure plan may include alternative surgical steps for the recommended surgical tasks. The patient specific procedure plan may provide alternative options for HCPs to select and/or give feedback on. Options that are not relevant to the patient and/or options that may lead to unsuccessful outcomes, may be determined and excluded from the patient specific procedure plan.

Recommended surgical tasks/steps may be determined for the patient specific procedure plan. The recommended surgical tasks/steps may be determined, for example, based on the determined outcomes (e.g., predicted outcomes) associated with the patient specific surgical steps/tasks. The recommended surgical tasks/steps may be the surgical tasks/steps that are associated with a higher predicted outcome success. For example, the populated patient specific procedure plan may include the surgical tasks associated with the highest predicted successful outcome. The recommended surgical task/steps may be the surgical tasks/steps associated with the facility information (e.g., staffing information, tool availability, OR availability, etc.). The recommended surgical task/steps may be the surgical tasks/steps associated with surgeon preferences.

A user (e.g., HCP) may provide input to the patient specific procedure plan, for example, as shown at 50250. For example, an HCP may select an alternative option for a surgical task (e.g., instead of the recommended surgical task). The tasks following the selected alternative option may be affected by the selection, for example, if choosing the alternative task changes how the procedure (e.g., rest of the procedure) can be performed. For example, if the recommended surgical task uses a first surgical tool and the HCP selects the alternative surgical task using a second surgical tool, subsequent surgical tasks using the first surgical tool may be altered (e.g., to consider the use of the second tool). The subsequent surgical tasks may not necessarily need to adapt to the selection of the alternative surgical task option. As shown at 50255, the patient specific procedure plan may be adjusted. The patient specific procedure plan may be adjusted, for example, based on the user input and/or in accommodation of a previously revised surgical task/step.

The HCP input may act as an override to the automated population of the patient specific procedure plan. HCPs may still control how the planned surgical procedure can be performed. For example, the patient specific procedure plan may be used as a baseline (e.g., so the HCP can see the potential strategies and/or options for the surgical procedure). The automated population of the patient specific procedure plan may reduce the workload of the HCPs. The HCPs may focus on selecting the preferred surgical tasks/steps rather than parse through the presurgical data and/or facility information to determine a surgical procedure plan.

The patient-specific procedure plan and/or adjusted patient specific procedure plan may be generated, for example, for the surgical procedure. As shown at 50260, the generated patient specific procedure plan may be displayed. The patient-specific procedure plan may be displayed, for example, as a viewable report (e.g., single viewable report). The patient-specific procedure plan may be sent to a surgical control system. The surgical control system may instruct surgical instruments and/or surgical systems, for example to carry out surgical tasks autonomously (e.g., based on the patient-specific procedure plan). For example, the surgical control system may determine parameters for a surgical instrument to use during a surgical procedure based on the patient-specific procedure plan.

Figure 14:
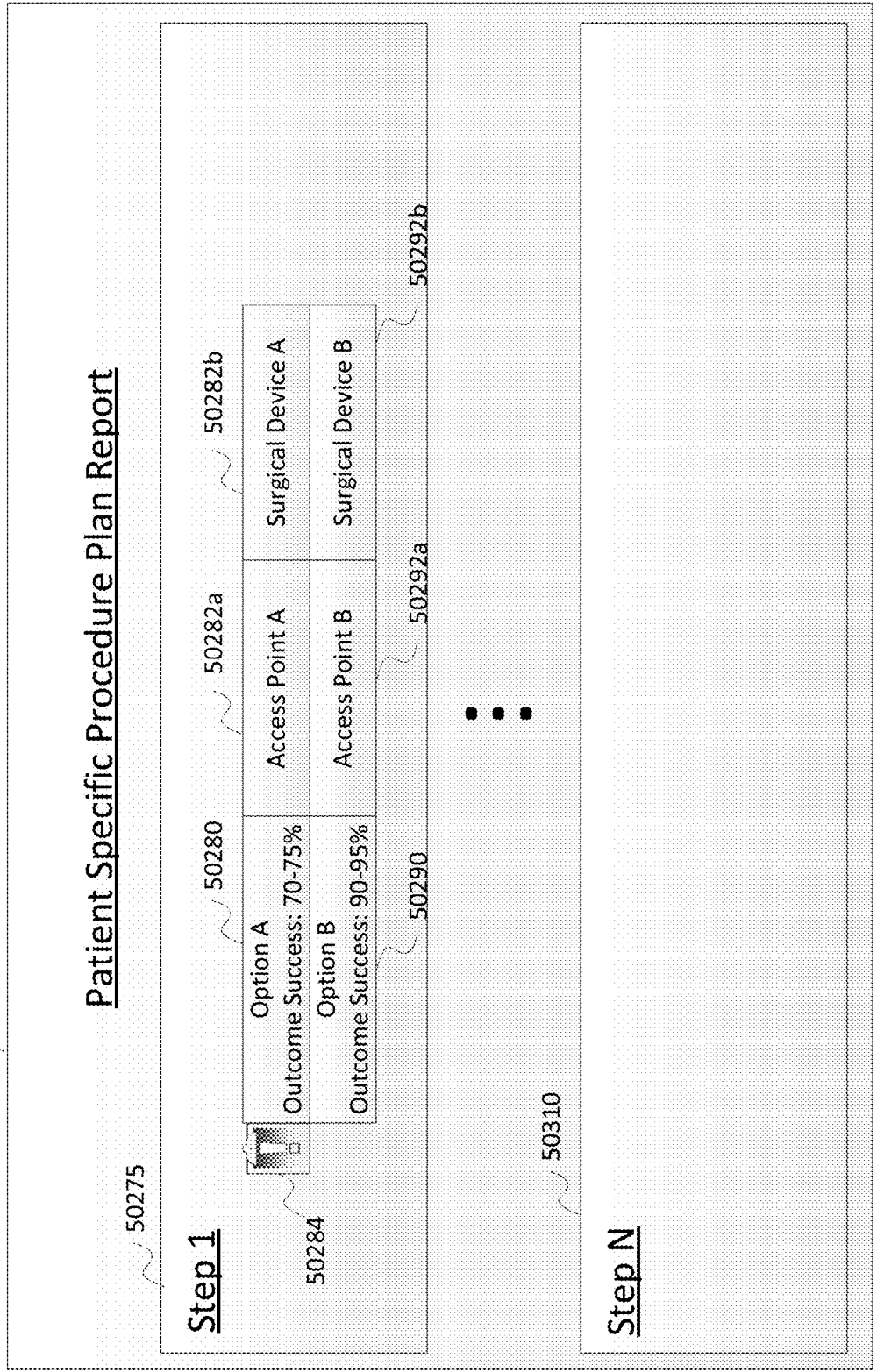
FIG. 14 illustrates an example of a patient specific procedure plan report.

FIG. 14 illustrates an example of a patient specific procedure plan report. The patient specific procedure plan report 50270 may include the surgical procedure steps for a patient specific surgical procedure. The surgical procedure steps may include Step 1 50275 through Step N 50310, for example. The surgical procedure steps may include surgical tasks. The surgical tasks may include a recommended surgical task and/or one or more alternative surgical tasks.

For example, Step 1 50275 may include multiple surgical task options. Step 1 50275 may include Option A 50280 and/or Option B 50290. Option A 50280 may be associated with a first outcome success (e.g., predicted outcome success), which may be the range between 70-75%. Option B 50290 may be associated with a second outcome success, which may be the range between 90-95%. Option A 50280 may use Access Point A 50282*a* and/or Surgical Device A 50282*b*. Option B 50290 may use Access Point B 50292*a* and/or Surgical Device B 50292*b*. Option A 50280 may be flagged, for example, if the surgical task is associated with incomplete and/or conflicting information/data. For example, Option A may have been determined using data/information that may be incomplete and/or conflicting. As shown at 50284, Option A 50280 may be flagged indicating the HCP to review the data/information. For example, the HCP may provide the missing data/information and/or verify the conflicting data/information. The outcome success associated with Option A may be revised based on the HCP input.

The patient specific procedure plan report may be interacted with (e.g., by an HCP). For example, an HCP may select one or more surgical tasks for a surgical step. The selection may affect the subsequent surgical tasks/steps in the surgical procedure. For example, a selection of a surgical task in Step 1 50275 may affect surgical task options in subsequent steps, such as Step N 50310, for example.

The patient specific procedure plan may include the recommended starting point, surgical tasks, and/or alternative surgical tasks for the surgical procedure. The patient specific procedure plan may include (e.g., an aggregation of) potential complications, an identification of auxiliary information, and/or the like. The patient specific procedure plan may include an identification of a relationship (e.g., an interaction) between procedure steps and the aggregated patient data. The patient specific procedure plan may include an initial access port location identification (e.g., to improve surgical site access), for example, which may be determined based on the procedure step, instrument selection, and/or patient data.

For example, the patient specific procedure plan may include an aggregation of the potential complications and/or identification of auxiliary information. For example, the patient specific procedure plan may include highlights and/or notations indicating identified co-morbidities that may interact, for example, during the surgical procedure. Complications may be determined, for example, such as identifying that co-morbidities may amplify the effects of each other and/or affect treatments that may be selected. Interactive disease states may be calculated and/or indicated, for example, that may increase the probability of complications.

The patient specific procedure plan may include an indication associated with a marginal biomarker. The indication associated with the marginal biomarker may be related to an identified disease state.

The patient specific procedure plan may include a notification associated with procedural steps that may be impacted and/or may be altered. The procedural step may be determined to be impacted and/or indicated to be altered, for example, based on one or more of the following: the determined disease, the state of the disease's advance, situational awareness of the HCP, facility, and/or staff, and/or the like.

The patient specific procedure plan may include an indication (e.g., highlight) associated with an identification of a metallic object. For example, a metallic object (e.g., clip, staple, buttress, etc.) may be detected. The patient specific procedure plan may include an indication (e.g., on an image and/or scan) that may indicate the location (e.g., relative location) of the metallic object. The indication may indicate areas where a surgical tool/device (e.g., ultrasonic device and/or radio frequency bipolar instrument) may interact poorly (e.g., harm the patient and/or not function properly), for example, due to the metallic object. The patient specific procedure plan may include a suggestion of a procedural step option to avoid the metal. The patient specific procedure plan may include a suggestion of alternative instrument(s) to use in the high metal areas. The patient specific procedure plan may include an adaptability of an energy algorithm and/or an integrity test (e.g., to improve detection) before adverse events occur and/or to verify integrity after passing through an area.

The patient specific procedure plan may include an indication indicating a relationship (e.g., interaction) between procedure steps and the patient specific surgical data. For example, the relationship (e.g., interaction) between procedure steps and the patient specific surgical data may be identified. A patient may be scheduled for a surgical procedure, such as a colorectal sigmoid resection (e.g., for Crohn's disease, which may refer to a chronic condition associated with inflammation). Chron's disease may affect and/or be related to (e.g., interact with) patient biomarkers and/or physiologic aspects. The co-morbidities may be affected. The co-morbidities of the patient data and/or therapies (e.g., blood pressure, blood sugar, blood thinners, pain reliever, etc.) may have physiologic effects that may (e.g., have the potential to) impact (e.g., interact with) device choices, device setups, or procedure steps. The procedure plan may be adapted based on the relationship (e.g., interaction). For example, the patient specific procedure plan may indicate a recommendation to adapt the procedure plan based on the relationship (e.g., interaction).

The patient specific procedure plan may include an access port location (e.g., initial access port location). An access port location (e.g., for a surgical procedure) may be identified, for example, based on the patient specific surgical data, instrument selection, surgical procedure step, and/or the like. The surgical site access may be improved, for example, based on the access port location. The access port location may be associated with a location on the patient and/or an angle of a surgical device being used at the surgical access site.

The patient specific procedure plan may indicate an amount of access, for example, for one or more pre-selected access ports (e.g., the amount of access each pre-select access port may provide). The patient specific procedure plan may indicate an interaction overlap for instruments used in an area, for example, based on trocar locations. The patient specific procedure plan may include an overlay of the patient specific data and/or images on the populated procedure plan. The patient specific procedure plan may indicate the trocar location(s). The patient specific procedure plan may indicate access capabilities, for example, based on the combination of the patient specific surgical data.

Figure 15:
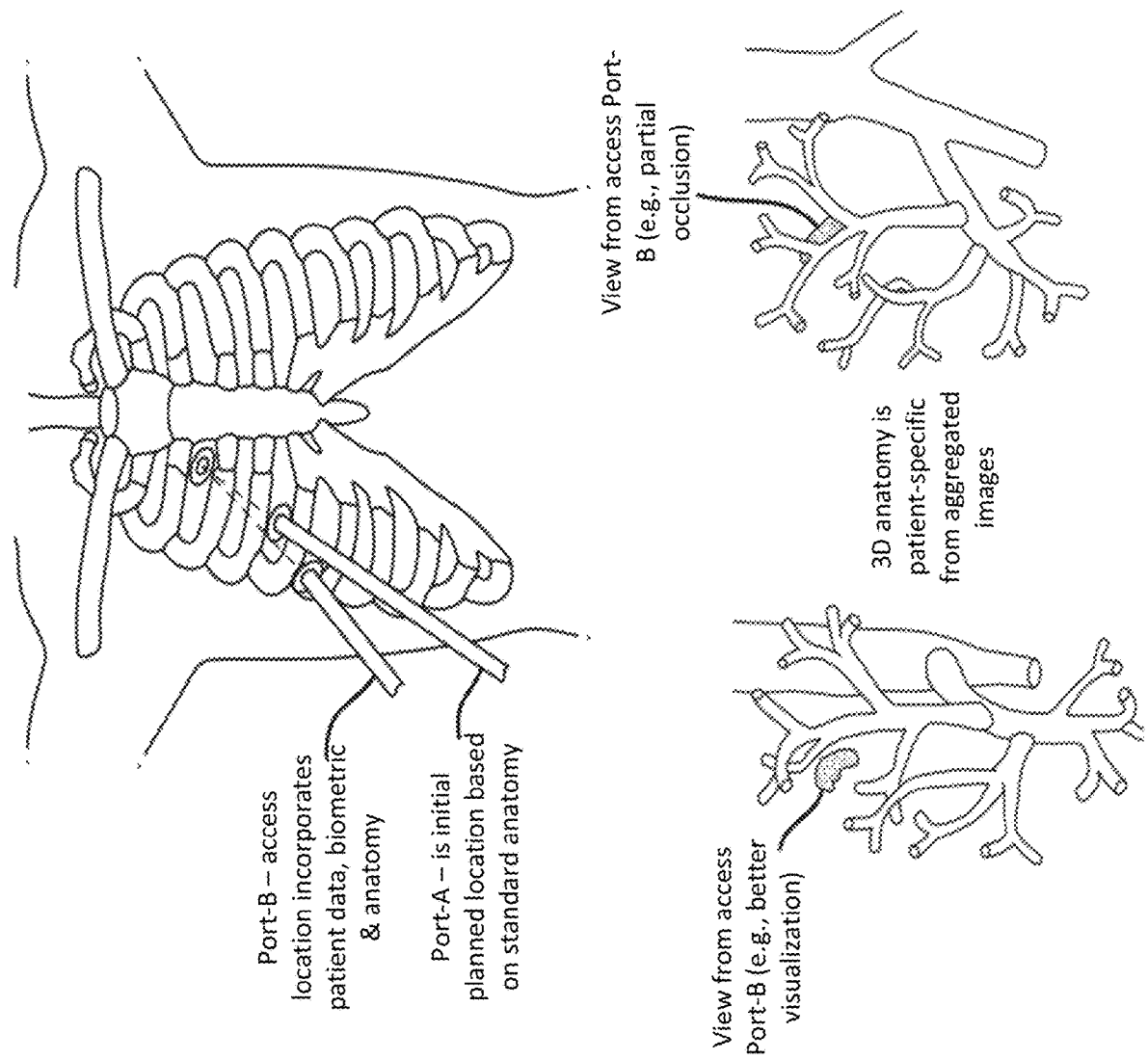
FIG. 15 illustrates an initial access port location identification.

FIG. 15 illustrates an initial access port location identification. For example, access ports may be identified. As shown in FIG. 15, a first access port (e.g., Port A) and a second access port (e.g., Port B) may be identified. The access ports may be determined based on a standard human anatomy. The access ports may be determined based on the standard human anatomy and/or the patient specific surgical data (e.g., biometric data and/or pre-surgical imaging of the patient's anatomy). The patient specific procedure plan may indicate a view of the patient, the surgical site, and/or access ports. The patient specific procedure plan may indicate occlusion (e.g., partial occlusion), for example, based on the patient specific surgical data/images. The patient specific procedure plan may include an anatomy image (e.g., 3D anatomy), which may be patient specific from aggregated images. The patient specific procedure plan may indicate the planned access port, for example, through the rib cage for instruments and/or a camera. The patient specific procedure plan may include an image with an overlay that may show an alternative access port approach, for example, that may provide additional access and/or visualization (e.g., to see occluded areas and/or better access of a tumor).

Figure 16:
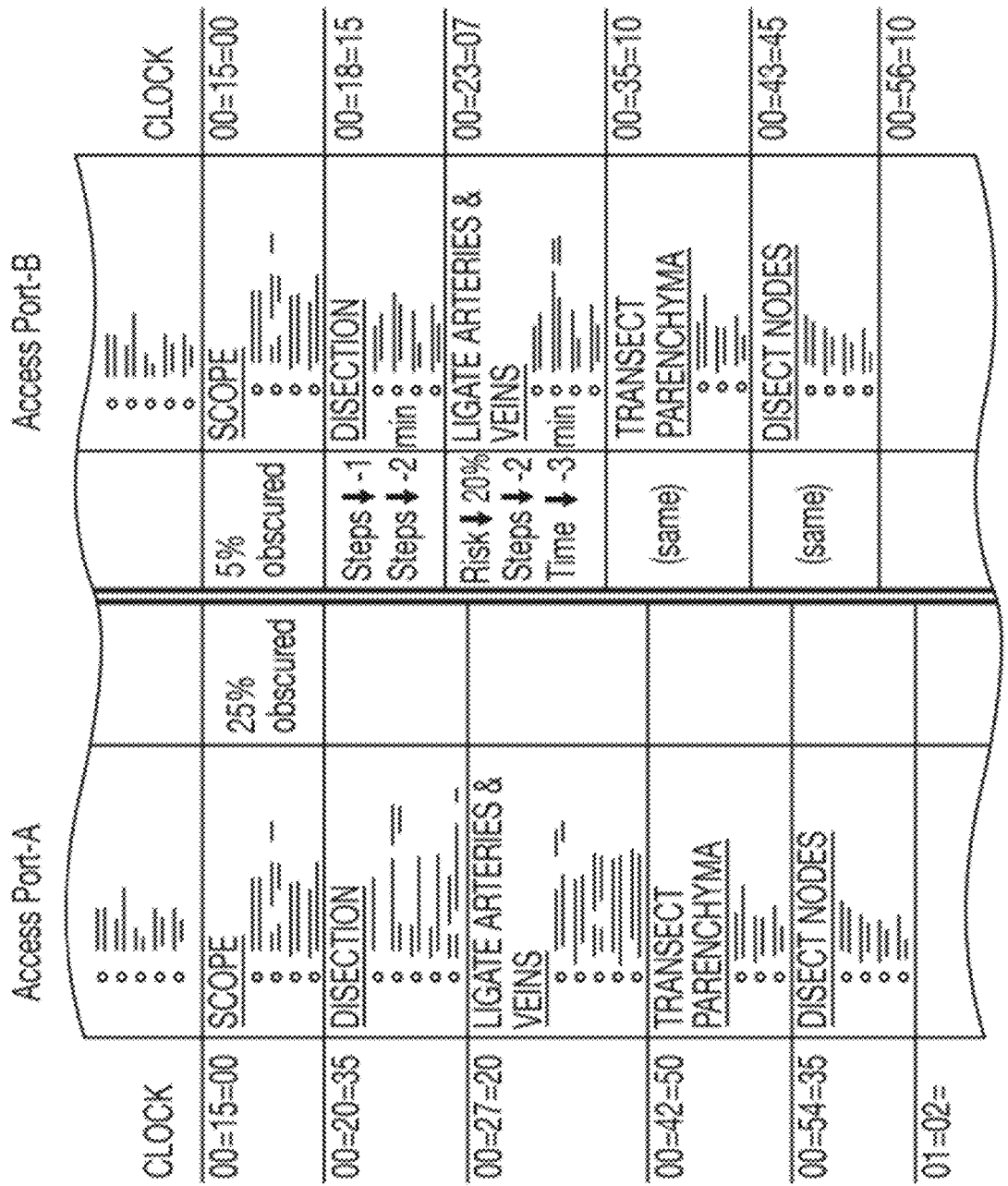
FIG. 16 illustrates an example overlay of patient data and imaging on a procedure plan.

FIG. 16 illustrates an example overlay of patient data and imaging on a procedure plan. As shown in FIG. 16, the patient specific procedure plan and/or the overlay may indicate surgical procedure steps that may be affected. The surgical procedure steps may be affected based on the selected access port. For example, using different access ports may change the surgical procedure plan. The overlay may be used to indicate surgical procedure steps that are affected by poor access ports.

Instrument positioning and/or access envelopes may be determined. The instrument positioning and/or access envelopes may be determined, for example, based on the patient specific surgical data and/or surgical procedure templates. The instrument movement envelope inside (e.g., end-effector, shaft) and/or outside (e.g., shafts, shrouds, robotic arm) the patient wall may be forecasted. The instrument positioning and/or access envelopes may be displayed. For example, the instrument positioning and/or access envelopes may be included in the patient specific procedure plan.

Identification of robotic aspects (e.g., outside the patient) may be automated. The interaction of the robotic aspects may be determined (e.g., automatically). For example, the identification may be performed using the patient specific surgical data, surgical procedure steps, surgical procedure baseline/template, and/or surgical device/tool selection. Conflicts (e.g., potential conflicts) and/or collision may be determined (e.g., as a baseline). Alternative access port locations may be indicated, for example, based on the potential conflicts and/or collisions. Alternative access port locations, patient positions, instrument mixes, and/or the like may be determined (e.g., and highlighted), for example, to minimize determined complications.

Optimal instrument positioning and/or access envelopes may be determined, for example, such that improper interactions (e.g., sword fighting) of shafts inside the patient's body (e.g., as the HCP interacts with the surgical site) is minimized. The determined instrument positioning and/or access envelopes may be determined, for example, to prevent handle, arm and/or shroud collisions (e.g., based on the interaction of the access port location, procedural step, and/or patient specific surgical data).

The patient specific procedure plan may be determined (e.g., automatically determined), for example, based on facility information. Facility information may include surgical tool availability, surgical device availability, inventory stock, surgical equipment availability, staffing, facility room availability, and/or the like. The facility information may be used to adjust the patient specific procedure plan. For example, the patient specific procedure plan may indicate to use a first surgical tool during the surgical procedure, but the first surgical tool may not be available (e.g., not sterilized, down for repair/maintenance). The patient specific procedure plan may be adjusted to use a second surgical tool (e.g., alternative surgical tool) in place of the first surgical tool. The patient specific procedure plan may be adjusted (e.g., subsequent tasks/steps in the procedure plan may be adjusted) based on the adjusted use of the second surgical tool.

The computing system may perform verification (e.g., automatic verification) with the planned surgical procedure. For example, an automated verification may be performed for the instrument needs, the procedure date, the facility usage, the shipments being received associated with surgical tools/consumables used for the surgical procedure, and/or the like. The computing system may determine (e.g., automatically determine) issues associated with the planned surgical instruments to be used in the surgical procedure.

A scheduling time for the surgical procedure may be determined, for example, based on the patient specific procedure plan. The computing system may determine a scheduling time based on the instruments selected in the patient specific procedure plan, staffing availability, facility availability, and/or the like. For example, the scheduled time may be a time when the selected instruments are available (e.g., mostly available, all available).

Devices/consumables may be ordered, for example, based on the inventory information and the devices/consumables that are selected to be used in the surgical procedure. For example, the computing system may determine that surgical consumables are to be used in the surgical procedure and may determine that the inventory is running low. The computing system may order replacement/extra consumables for the surgical procedure, for example, in the case that the replacement/extra consumables are used (e.g., needed) to complete the procedure.

The patient specific procedure plan may include an indication associated with facility inventory and surgical devices selected for the surgical procedure. The indication may indicate inventory alternatives (e.g., inventory that may be used instead of the selected inventory in the surgical procedure plan). The indication may highlight surgical devices that may be missing/unavailable (e.g., in the facility) that were selected for the surgical procedure.

The computing system may determine the patient specific procedure plan based on facility information and/or other surgical procedure being planned. Medical facilities perform many surgical procedures, and the surgical procedures may occur simultaneously and/or overlap in time. Surgical devices may be used in more than one surgical procedure. A surgical device and/or consumable may have already been selected for a surgical procedure, and therefore may not be used in a different surgical procedure occurring at the same time. The computing system may consider (e.g., in determining the patient specific procedure plan) other surgical procedures being planned. The computing system may interact with other users planning procedures that may use the same staffing/personnel and/or instruments. The computing system may prioritize surgical procedures. For example, a first surgical procedure may be prioritized over a second surgical procedure. The first surgical procedure may have a priority in device selection and/or consumable selection. The prioritization may be performed based on a requirement associated with the surgical procedure, a risk level associated with the surgical procedure, and/or the like.

In examples, a surgeon may develop a baseline surgical procedure plan/map. The baseline plan may include the surgical devices to be used in the procedure. The computing system may determine (e.g., based on facility information and the baseline plan), that a selected surgical instrument (e.g., an Echelon 60) is not available in stock. The computing system may indicate that the surgical instrument is not available for the procedure. The computing system may indicate an alternative surgical instrument (e.g., Echelon 45), for example, that may be available. The computing system may indicate to the surgeon that the selected surgical instrument is not available and recommend the alternative surgical instrument. The surgeon may accept or deny the recommendation. The computing system may update the baseline procedure plan, for example, if the surgeon accepts the recommendation to use the alternative surgical instrument. The baseline procedure plan may be updated to accommodate the use of the alternative surgical instrument (e.g., instead of the selected surgical instrument). For example, the baseline procedure plan may be adjusted such that the procedure step may include the possibility of extra firings from the alternative stapler (e.g., to accommodate the differences in the two surgical devices). The computing system may indicate that the adjusted baseline procedure plan has been adjusted to increase a number of cartridges (e.g., to compensate for the difference with the alternative surgical instrument). The computing system may indicate to the surgeon a cartridge color selection for the extra firings. The computing system may update the baseline procedure plan (e.g., if the surgeon accepts the modifications), and may order the additional supplies based on the changed procedure plan. The computing system may verify that the additional approach (e.g., extra firings using the alternative surgical tool) is acceptable from a risk perspective.

The patient specific procedure plan may be determined, for example, based on room, patient, and/or staff availabilities. The patient specific procedure plan may overlay room, patient, and/or staff availabilities on a baseline procedure plan. The patient specific procedure plan may include follow-ups based on the room, patient, and/or staff availabilities. For example, automatic patient scheduling for the procedure and/or follow-ups may be performed.

For example, the computing system may perform scheduling correlation (e.g., automated scheduling correlation) for the facility rooms, equipment, personnel, and/or surgeon availability. The computing system may determine a time (e.g., optimal time) for the planned procedure, for example, based on the surgical procedure (e.g., acute critical need of the procedure). For example, the computing system may consider whether a planned surgical procedure is urgent. The computing system may perform escalation associated with a surgical procedure timing and/or scheduling, for example, based on the patient needs and/or other planned procedures. The computing system may aggregate the patient's scheduled treatments, for example, to determine a comorbidity implication associated with the planned surgical procedure. The computing system may consider pre-operative patient progress to predefined goals (e.g., weight loss), for example, as a trigger to change procedure scheduling. The computing system may update patient biomarkers and/or patient examination of patient health from monitoring HCPs (e.g., surgeon, primary care physician, pharmacist, physical therapist, and/or the like). The computing system may perform a comparison (e.g., automatic comparison) between patients (e.g., patients of other scheduled procedures), that may impact and/or create a conflict with the current scheduling. The computing system may propose changes to scheduling of the surgical procedures, for example, to resolve the determined conflicts.

The computing system may perform procedure scheduling based on personnel availability and/or scheduling. The computing system may consider the availabilities of the HCPs, for example, including the anesthesiologist, assistant physician, back table nurse specialist, oncology/imagine specialist, a technician, a urologist, and/or the like.

Systems, methods, and instrumentalities are disclosed for identification of image shapes based on situational awareness of a surgical image and annotation of shapes or pixels. A surgical video comprising video frames may be obtained. Surgical context data for a surgical procedure may be obtained. Elements in the video frames may be identified based on the surgical context data using image processing. Annotation data may be generated for the video frame, for example, based on the surgical context data and the identified element(s).

Elements within a surgical video may be identified, for example, by a surgical computing system. For example, image shapes may be identified in the surgical video, and the image shapes may be linked to surgical elements. For example, the image shapes may be identified as structures, organs, features, and/or other elements in a surgical procedure. For example, an image element may be identified as a lung, tumor, blood, artery and/or other anatomical elements. Features associated with the elements may be identified. The identified features may include, for example, one or more of the following: status, condition, type, tissue type (e.g., fat, fat and vessel, duct, organ, fat and organ, connective tissue, etc.), tissue condition (e.g., inflamed, friable, calcified, edematous, bleeding, charred, etc.), and/or the like.

The identification of such elements and/or features may be performed, for example, using image processing on the surgical video (e.g., a surgical video frame) and using situational awareness associated with the surgical image. Situational awareness may be accomplished using surgical context data and/or surgical procedure data obtained via a situational awareness system (e.g., as described herein with respect to FIG. 7). Annotation data may be determined based on the identified elements. The annotation data may be inserted into the surgical video.

A surgical video or surgical video frame may be parsed into grouped elements and/or groups of pixels. Throughout a surgical video, the elements may exhibit movement, behavior, and/or outcomes (e.g., surgical events, such as bleeding). The elements may be tracked between surgical video frames (e.g., consecutive frames) in the surgical video. Tracking data (e.g., behavior, movement, and/or outcome data) may be determined, for example, using the surgical context data and the identified elements. The tracking data may be included in the annotation data and inserted into the surgical video. The tracking data may be used for verification of anticipated movements, behaviors, and/or outcomes.

The surgical computing system may perform annotation of pixels within an image. The annotation of pixels may be used for machine learning, object identification, object tracking, self-identification, and/or the like. The annotation may include situational identification and annotation of individual pixels and/or groups of pixels in the surgical video.

Figure 17:
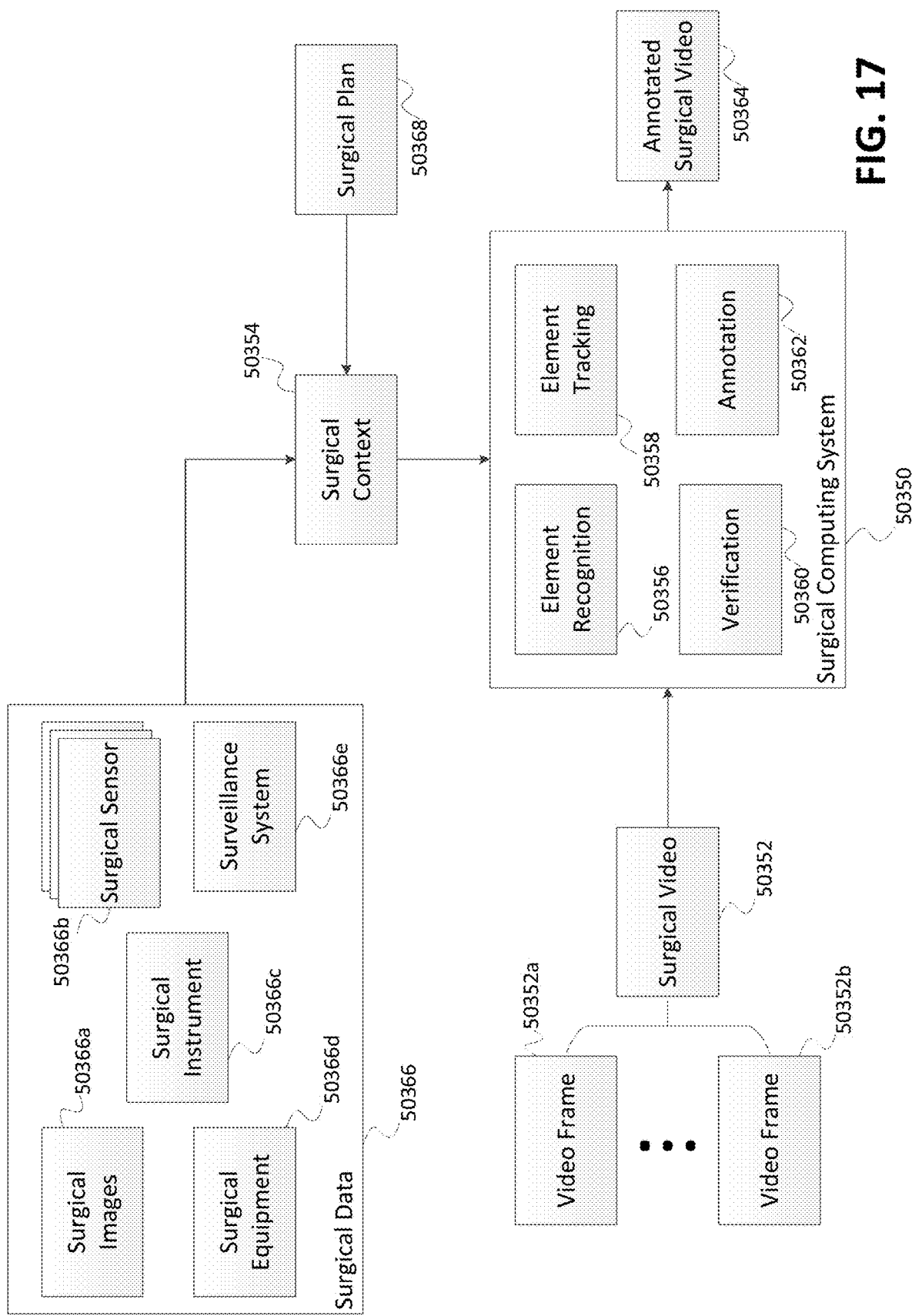
FIG. 17 illustrates an example of annotating surgical video using situational awareness.

FIG. 17 illustrates an example of annotating surgical video based on situational awareness of the surgical image. As shown in FIG. 17, a surgical computing system 50350, which may be the surgical hub 20006 as shown in FIG. 1, may obtain a surgical video 50352 and a surgical context 50354 (e.g., surgical context data).

The surgical context 50354 may indicate a surgical procedure, a surgical event, a surgical step, a surgical phase, a surgical task, a complication, and/or the like. The surgical context 50354 may be determined. For example, the surgical context 50354 may be determined using situational awareness (e.g., as described herein with respect to FIG. 7).

As shown, the surgical context 50354 associated with the surgical video and/or surgical procedure may be determined, for example based on surgical data 50366 (e.g., surgical procedure data). The surgical data 50366 may be surgical data generated before, during, and/or after a surgical procedure. For example, the surgical data 50366 may be the surgical procedure data 50020 as shown in FIG. 8. The surgical data 50366 may include surgical data generated from surgical systems, such as, for example, surgical images 50366*a*, surgical sensor(s) 50366*b* (e.g., wearables), surgical instrument(s) 50355*c*, surgical equipment 50366*d*, surveillance system(s) 50366*e*, and/or the like.

The surgical context 50354 may be determined, for example, based on the surgical data 50366 and a surgical plan 50368 (e.g., surgical procedure plan). The surgical plan 50368 may include information associated with a surgical procedure, such as, for example, the surgical procedure steps, surgical procedure tasks, surgical instruments used, surgical equipment used, and/or the like. The surgical plan 50368 may be a patient-specific surgical procedure plan (e.g., as described herein with respect to FIGS. 11, 14, and 16). The surgical context 50354 may be a patient-specific surgical context for the surgical procedure. The surgical context 50354 may be determined, for example, based on the patient's specific anatomy and/or medical records.

The surgical context 50354 may indicate a surgical procedure step, for example. The surgical procedure step may be associated with performing an incision on a portion of a lung. The surgical context 50354 may include information associated with the surgical instruments used, surgical equipment used, the organs in the surgical site, features in the surgical site, and/or the like. The surgical context 50354 may be used to guide the surgical procedure.

As shown in FIG. 17, the surgical computing system 50350 may obtain a surgical video 50352. The surgical video may be composed of video frames (e.g., surgical video frames), for example, such as video frame 50352*a* and video frame 50352*b*. The surgical video may be a video of the surgical procedure.

The surgical computing system 50350, which may be the surgical hub 20006 as described in FIG. 1, may perform element recognition and/or element identification, as shown at 50356. The surgical video may be associated with an endoscopic surgery (e.g., inside the body video). For example, the surgical video may capture video inside a patient's body during the surgical procedure. The surgical video may capture video showing elements inside the patient's body, such as, organs, structures, features, anatomy, surgical instruments (e.g., a portion of a surgical instrument, for example, such as a tip, jaw, knife, end effector, etc.), tissue, tumors, arteries, veins, bronchus, and/or the like. The elements inside the patient's body may be identified.

Element identification and/or element recognition may be performed based on the surgical context 50354 and situational awareness (e.g., as described herein), for example, using image processing (e.g., as described herein). As described herein, the surgical context 50354 may provide context for the surgical procedure and/or elements identified in a surgical video during the surgical procedure. For example, a surgical context 50354 may provide information associated with a lung surgical procedure. The surgical context 50354 may be used to identify elements in a surgical video, such as a lung. The surgical context 50354 may be used to distinguish elements in a surgical video from other similar elements. For example, organs may share a similar shape in a surgical video, but with the surgical context, the proper organ may be identified. For example, during a lung surgical procedure, the surgical context may be used to identify the element as a lung rather than the element being a different organ with a similar shape as lungs. For example, the surgical context 50354 may indicate that a particular surgical device is being used, which may be used to identify the surgical device or a portion of the surgical device in a surgical video frame(s).

The surgical computing system 50350 may identify elements in the surgical video 50352. The surgical computing system 50350 may perform element identification and/or element recognition on the surgical video 50352, for example, by using the video frames. The surgical computing system 50350 may perform element identification and/or element recognition on each video frame, for example, such as a first video frame (e.g., the video frame 50352*a*) and a second (e.g., subsequent or previous) video frame (e.g., video frame 50352*b*). The video frames may be processed to identify elements within each video frame.

The surgical video 50352 and/or video frames may be composed of pixels. The elements in the video frames may be composed of groups of pixels, for example. A first group of pixels may be clustered and identified as making up a first element in the video frame. The surgical computing system 50350 may determine the first group of pixels associated with the first element. The identified element(s) may be comprised of a respective group of pixels. The identified element(s) may be separated into sub-elements that comprise the respective element. The sub-elements may be comprised of sub-groups of pixels associated with each sub-element.

The surgical computing system may use one or more selection methodologies, for example, to identify elements in a surgical video. The selection methodologies may be associated with using one or more of the following: a bounding box; a polygon; a point (e.g., keypoint); a cuboid; semantic segmentation; etc.

For example, the surgical computing system may use a bounding box selection methodology to identify elements in a surgical video. A bounding box selection methodology may be associated with using a rectangular structure to match the element. For example, the rectangular structure may relate to x (min)/y (min) and x (max)/y (max). The bounding box may enable detection and/or recognition of objects of differing classifications. The boxes may be anatomically located, for example, corresponding to the expected location organs, structures, and/or tissues (e.g., based on the identification of key landmarks, such as, for example, other organs, structures, and/or tissues). For example, differentiation between elements of similar shapes may be enabled (e.g., differentiation of the stomach from the liver), for example, regardless of the shape and/or color similarity. The boxing (e.g., automatic boxing) may enable the surgical computing system to define the differences (e.g., between elements of similar shape and/or color), for example, using limited processing in a gross approach.

For example, the surgical computing system may use a polygon selection methodology to identify elements in a surgical video. A polygon selection methodology may be associated with using a series of selected points that when used together may create a poly structure that may enable a classification differentiation. For example, the points may be a perimeter of an element. The points may be a perimeter based on one or more of a color, texture, a morph of multi-spectral imaging with visual imaging, etc. The number of points defining the polygon may increase processing and/or selection timing.

For example, the surgical computing system may use a cuboid selection methodology to identify elements in a surgical video. A cuboid selection methodology may be associated with using a box (e.g., three-dimensional box) selection that enables for multi-dimensional viewing.

For example, the surgical computing system may use a semantic segmentation selection methodology to identify elements in a surgical video. The semantic segmentation selection methodology may be associated with pixel by pixel tissue semantic annotation of the tissue (e.g., all the tissue). An overlay of where the elements (e.g., organs and/or tissue) may be generated. How to anticipate the elements may be determined. In examples, each pixel and/or group of pixels may be annotated and/or labeled as to what element the pixel is associated with.

The surgical computing system may identify (e.g., automatically identify) that the selection methodology used for the element identification is inappropriate (e.g., inaccurate). For example, the surgical computing system may use a baseline approach that is predefined. For example, if a threshold amount of irregularities and/or discrepancies are identified using a selection methodology, the surgical computing system may adjust (e.g., automatically adjust) the selection methodology. The surgical computing system may compare the results (e.g., between the different selection methodologies) and select the selection methodology that results in the least amount of resources used and/or least amount of false positives.

The surgical computing system may perform selection delineation. Selection delineation may be associated with instance segmentation and/or bordering. For example, the surgical computing system may perform instance segmentation associated with the identified elements. Instance segmentation may include taking an element and separating it into subsets of multiple instances. The elements in the surgical video 50352 and/or video frames may comprise sub-elements. For example, an element may be an organ (e.g., lungs) and the organ may have differentiable sections.

The identified element(s) may be separated into sub-elements that comprise the respective element. The sub-elements may be comprised of sub-groups of pixels associated with each sub-element. For example, the surgical computing system may identify an element to be the small intestines or jejunum. The jejunum may be separated into multiple anatomic sections (e.g., four anatomic quadrants). The surgical computing system may identify the overall structure of the jejunum. The surgical computing system may perform bunching of a quadrant group in the jejunum to define the four portions of the jejunum. The surgical computing system may use the differentiable portions of the jejunum to determine information associated with the video frame. For example, the surgical computing system may use the information associated with the differentiable portions to identify where the surgical system is viewing.

For example, the group of pixels associated with an element may be further divided into sub-groups of pixels. The sub-groups of pixels may compose the sub-elements. For example, a first sub-group of pixels may include the pixels that compose the left lung, and a second sub-group of pixels may include the pixels that compose the right lung. A first sub-group of pixels may include the pixels that compose a first lobe in the left lung, and a second sub-group of pixels may include the pixels that compose a second lobe in the left lung.

For example, lungs may be composed of a left lung and a right lung. The left lung may be differentiable from the right lung (e.g., the left lung may be smaller than the right lung and/or may be composed of a notch, for example, to give room for the heart). The lungs may be composed of (e.g., divided into) lobes. The lungs may be composed of five lobes. For example, the left lung may comprise two lobes, and the right lung may comprise three lobes. The lobes may be differentiable from each other. The surgical computing system may identify the sub-elements (e.g., lobes, left lung, and/or right lung) within an element, based on the surgical context data 50354.

The surgical computing system may use surrounding elements and/or features in the video frame, for example, to identify the lungs and/or sub-elements of the lungs (e.g., lobes). The surgical computing system may use the shape of the lungs, the ribcage, and/or other hard landmarks to orient itself, for example, and separate the different segments of the lungs. The user may section and/or review the portions of interest, and/or note the effects on the other portions.

The surgical computing system may perform bordering, for example, in the video frame, based on the surgical context data 50354. The surgical computing system may differentiate the tissues and/or organs, for example, from connective tissue background. The differentiation may be performed, for example, once a structure (e.g., element) is identified and/or selection and divided into instances. A border around the sub-elements (e.g., instances) may be defined. The object may be defined (e.g., self-defined), for example, based on the border. If the border is overlapped with a border of another segment, the shared border may be aligned between the organs and/or tissues, for example, to eliminate the overlap.

The surgical computing system may highlight and/or delineate the elements in the surgical video and/or video frame(s). Once the structures are identified and/or segmented, the surgical computing system may change the contrast and/or brightness of the video frame, for example, to accentuate elements and/or features in the frame. Objects of interest may be selected to be accentuated. The objects of interest may have the contrast and/or brightness changed, for example, to allow a user to differentiate between the objects of interest and other elements in the surgical video. Instances and/or sub-elements may be accentuated, for example, based on the surgical context data 50354.

The surgical computing system may determine characteristics and/or features associated with the identified elements. For example, the surgical computing system may determine the element identification. The surgical computing system may determine characteristics and/or features, such as, for example, one or more of the following: status, condition, type, tissue type (e.g., fat, fat and vessel, duct, organ, fat and organ, connective tissue, etc.), tissue condition (e.g., inflamed, friable, calcified, edematous, bleeding, charred, etc.) and/or the like.

As shown in FIG. 17, the surgical computing system 50350 may perform element tracking 50358. The surgical computing system may perform element tracking (e.g., object tracking) for example, for elements in the surgical video. Element tracking may include determining tracking information for elements in the video frames. For example, an element in a first video frame may be identified in a second video frame. A behavior, movement, and/or outcome may be determined for the element using the first video frame and second video frame. For example, the second video frame may show the element in a different location than the element was in the first video frame. Information about the element across video frames may be determined.

The surgical computing system 50350 may perform verification, for example, as shown at 50360. The verification may include verifying the identified elements and/or tracking. Element tracking and verification will be described in more detail with reference to FIG. 19.

As shown in FIG. 17, the surgical computing system 50350 may generate annotation data, for example, based on the performed element recognition, element tracking, and/or verification (e.g., as shown at 50362). The surgical computing system may determine annotation data for the surgical video and/or video frames. The computing system may determine annotation data for the surgical video and/or video frames, for example, using the identified elements in the video frames and the surgical context data. For example, the annotation data may include element identification information and/or element tracking information. The annotation data may include sub-element identification within the elements. The annotation data may include general information associated with the video frame, such as, for example, the surgical procedure step, surgical task, surgical event, and/or the like, associated with the video frame. The annotation data may include one or more of the following: element identification information, element grouping information, element subgrouping information, element type information, element description information, element condition information, surgical step information, surgical task information, surgical event information, surgical instrument information, surgical equipment information, and/or the like.

The annotation data may be generated based on a surgical event indicated in the surgical context. Event directed annotation (e.g., automatic annotation) may be performed. For example, annotation may be automated using the surgical computing system. Data flagging may be performed, for example by the surgical computing system or a sensor. For example, event directed annotation may be performed for a coupled surgical task, a coupled instrument, or instrument setup.

Event directed annotation may be performed which may be associated with micro-outcomes of a previous surgical step. For example, a previous surgical step may indicate bleeding. The event directed annotation may include determining annotation data to include the magnitude of the bleeding, a timing of the bleeding (e.g., how many frames the bleeding occurs for), a time associated with releasing from the primary surgical instrument, a secondary follow-up interventional surgical tool use, and/or the like.

Event directed annotation may be associated with determining out of body images. For example, the surgical computing system may be configured to redact (e.g., blank out) images that are detected to be out of body.

Event directed annotation may include inserting annotation data including local and/or global metadata. Local metadata may include lead up information, for example, information associated with neighboring video frames. Local metadata may include continuous variables and/or discrete variables. Global metadata may include information associated with the patient, instrument, procedure, surgeon, and/or the like. The metadata may be inserted into the surgical video.

Event directed annotation may include inserting annotation data associated with a response to an identified event. For example, a video frame may be associated with a surgical event. A response to the surgical event may be determined. An algorithm (e.g., querying algorithm) may be used to detect a resulting event. For example, charring may be detected. The annotation data may indicate to focus on the generator data, for example, to provide information on the detected event.

Annotation may be performed during a live surgical procedure and/or after a surgical procedure. Annotation data associated with complicated improvements to the surgical procedure may be performed after the surgical procedure. Live annotation may include simpler annotation and/or processing tasks. For example, live annotation may be performed to minimize the need for secure storage and/or processing of the live surgical procedure data.

Figure 18:
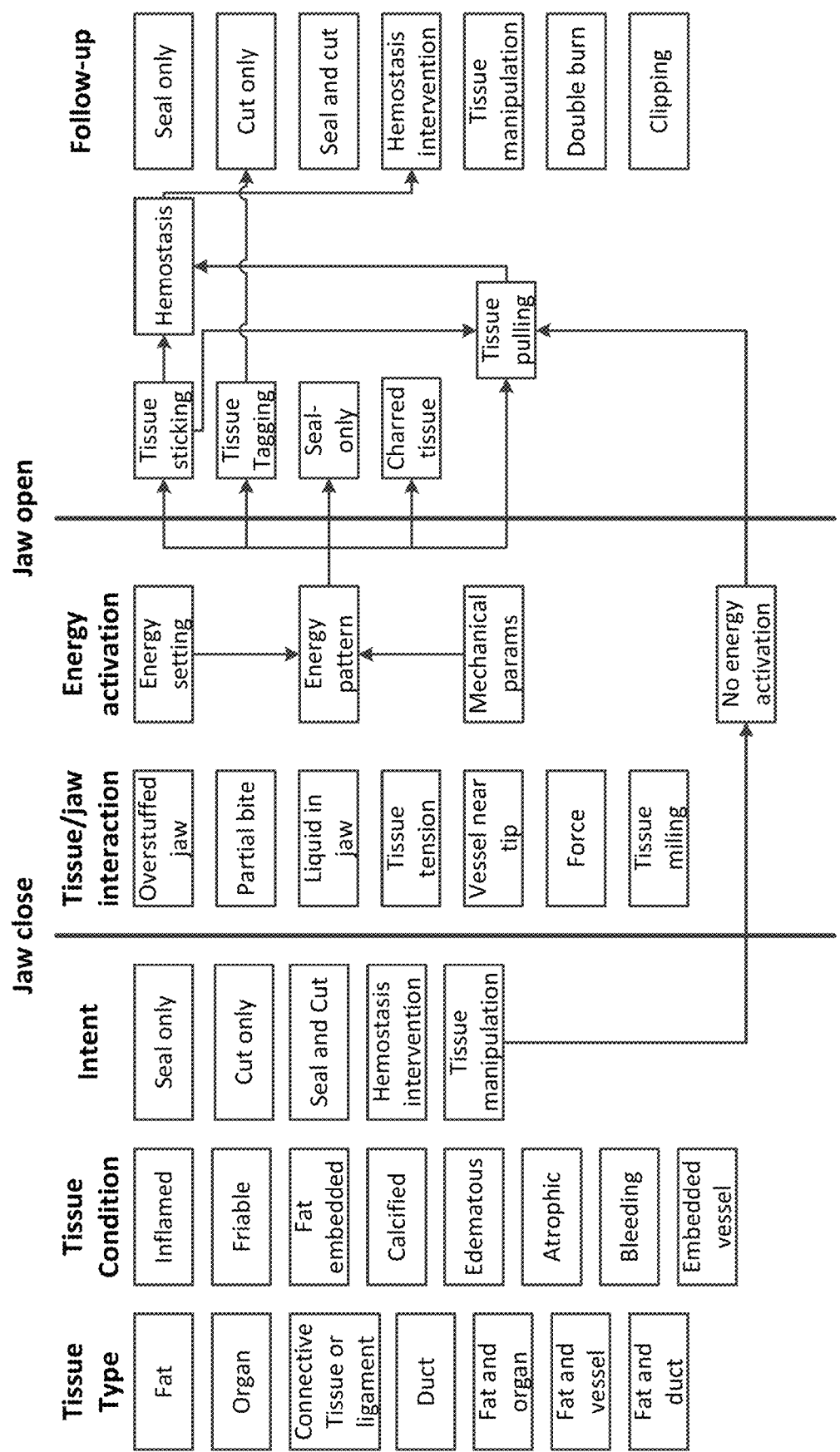
FIG. 18 illustrates example annotations associated with a surgical procedure.

Annotation may be guided by a surgical procedure map. FIG. 18 illustrates example annotations associated with a surgical procedure map. The surgical procedure map may be included in a surgical procedure plan. The surgical procedure map may indicate potential surgical steps and/or surgical outcomes associated with a surgical procedure. For example, the surgical procedure map may indicate potential characteristics associated with elements (e.g., organs, structures, and/or features) in the surgical procedure. For example, the surgical procedure map may indicate potential tissue types, tissue conditions, and/or procedure intents associated with a surgical procedure. The surgical procedure map may guide a surgical procedure. The surgical procedure map may be used as a dictionary, for example, to perform annotation of surgical video and/or video frames associated with a surgical procedure.

The surgical procedure map may indicate a surgical workflow. For example, the surgical procedure map may indicate potential outcomes associated with the surgical workflow.

In some examples, the annotation data may be inserted into the surgical video. The annotation data may be information associated with the frame itself and/or metadata associated with the surgical procedure and/or events. An annotated surgical video 50364 may be generated and output, for example, to surgical systems, storage, and/or the like. The annotation data may be inserted into the surgical video, for example, on the video frame level. The annotation data may be attached to the video frame. The annotation data may be inserted into the surgical video, for example, on a pixel level (e.g., pixel group level). For example, each pixel in a video frame may have respective annotation data inserted into the pixel. The annotation data for each pixel may include information identifying the element the pixel is associated with.

In examples, a group of pixels may be associated with lungs. The surgical computing system may identify the lungs and determine annotation data associated with the lungs. The surgical computing system may insert lung annotation data in the group of pixels associated with the lungs. The annotation data inserted into the group of pixels may include identification information, lung condition information, and/or the like. The surgical computing system may identify instances of the lungs (e.g., lobes of the lungs). The instances of the lungs may be composed of sub-groups of pixels. The surgical computing system may insert sub-element annotation data associated with the respective instances of the lungs in the associated sub-groups of pixels. For example, the surgical computing system may insert respective sub-element annotation data in the sub-group of pixels associated with a first lobe in the left lung. The sub-element annotation data inserted in the sub-group of pixels associated with the first lobe in the left lungs may include identification information that may indicate the sub-element.

In some examples, the annotation data may be used to generate control signal (e.g., indicating the determined control parameters), for example, to a surgical control system. In some examples, the annotation data may be stored and/or sent separately from the surgical video (e.g., to a surgical control system, to a surgical analysis system, etc.).

Figure 19:
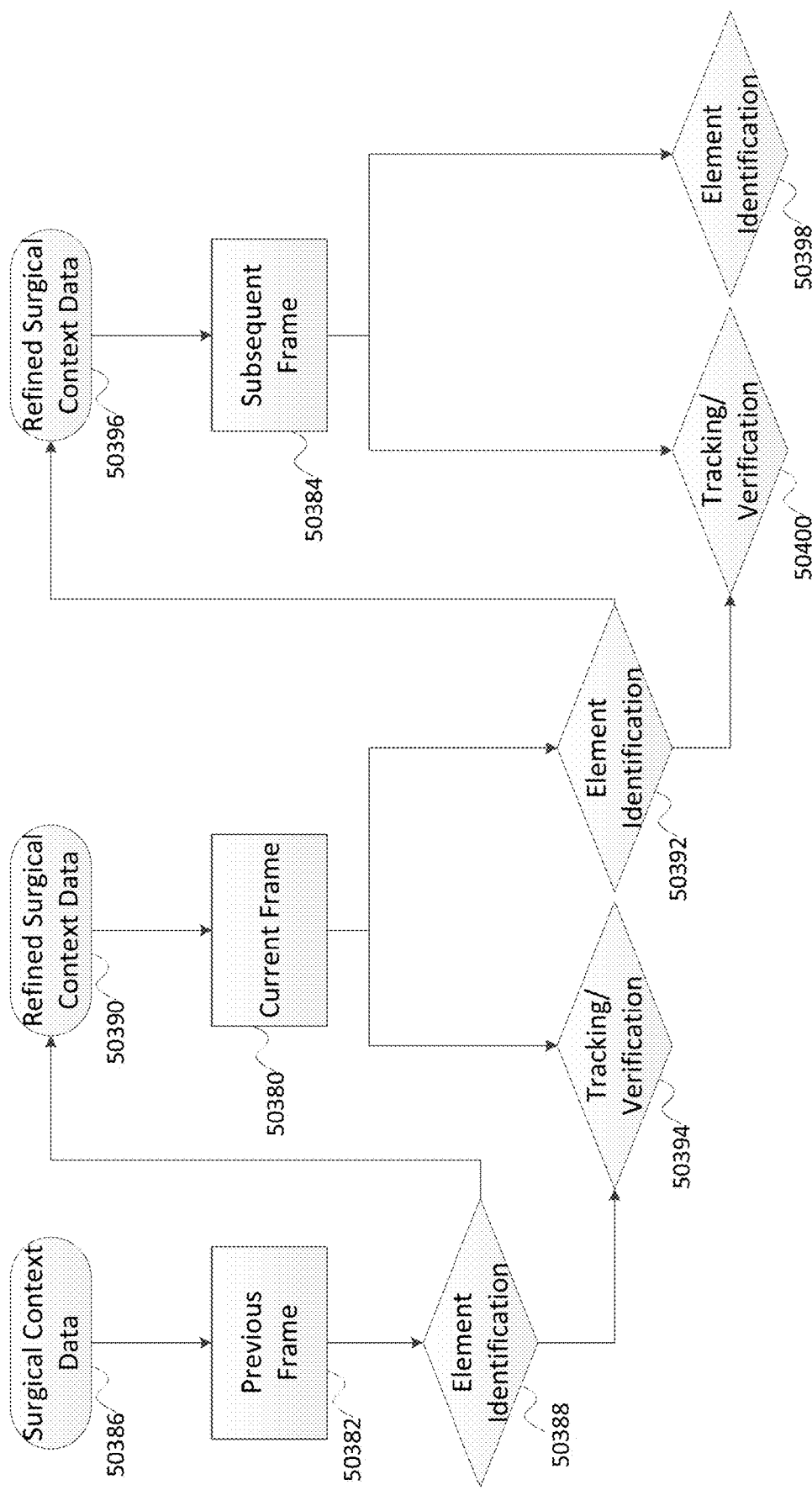
FIG. 19 illustrates an example of determining element tracking information and verification for elements in a surgical video.

FIG. 19 illustrates an example flow of determining element tracking information and verification for elements in a surgical video. The surgical video may include video frames. For a selected video frame, element tracking information and verification may be determined, for example, using a previous video frame(s). Element tracking information may be used for element tracking information and verification determination for subsequent video frame(s). As shown in FIG. 19, a current frame 50380 of the surgical video may be the frame that is temporally after a previous frame 50382 and comes before a subsequent frame 50384. The surgical computing system may perform element identification on the previous frame 50382 (e.g., as shown at 50388). The element identification on the previous frame may be performed based on surgical context data 50386 (e.g., as described herein).

The surgical context data 50386 may be refined and/or updated (e.g., as shown at 50390 in FIG. 19). For example, the surgical context data may be refined and/or updated based on the identified element(s) in a first video frame. Element(s) in a second video frame may be identified, for example, using the refined and/or updated surgical context data (e.g., using image processing). Annotation data for the second video frame may be determined using the refined surgical context data and the element(s) identified in the second video frame.

For example, the surgical context data 50386 may be refined and/or updated using the identified elements in the previous frame 50382. For example, the identified elements in the previous frame 50382 may provide additional information about the surgical context of the surgical procedure. The additional information may be used to verify the surgical context data. If there are discrepancies between the surgical context data and the identified elements, the surgical context data may be updated. For example, the surgical context data may indicate that a first surgical instrument is being used at a time associated with the previous frame 50382. The element identification information may indicate that a second surgical instrument is being used in the previous frame 50382 (e.g., instead of the first surgical instrument). The surgical context data may be refined and/or updated to be used in subsequent frames. The element identification information may indicate that the first surgical instrument is being used in the previous frame 50382 (e.g., same as the surgical context data). The surgical context data may be verified, for example, based on the confirming identification information.

The refined surgical context data 50930 may be used for element identification, element tracking, and/or verification for the current frame 50380. Element identification may be performed for the current frame 50380 (e.g., as shown at 50392), for example, using the refined surgical context data 50390 (e.g., as described herein). Element tracking and/or verification may be performed on the surgical video, for example, using the previous frame 50382 and the current frame 50380. Although not shown in FIG. 19, those skilled in the art would appreciate that element tracking information derived from a current video frame may be used to refine and/or update the element identification of previous video frame(s).

As shown at 50394, the element tracking and/or verification may be performed using the identified elements from the previous frame 50382 and the identified elements from the current frame 50380. Tracking information associated with a surgical video may be determined, for example, using multiple video frames. Elements identified in a first video frame and elements identified in a second video frame may be used, for example, to determine tracking data. The tracking data may be associated with element behavior, element movement, and/or outcome information (e.g., associated with the elements). The determined tracking data may be included in the annotation data.

For example, movement, behavior, and/or outcome information may be determined for the elements across the previous frame 50382 and the current frame 50380. An element in the previous frame 50382 may be identified as in a different location in the current frame 50380. Tracking data may be determined based on the movement of the element.

Differences in an element between the previous frame 50382 and the current frame 50380 may indicate a behavior of the element. For example, the element may be determined to be pulsing and/or exhibiting a repetitive movement across video frames. Repetitive movement of an element may be confirmed, for example, by tracking the element across video frames. Element identification may also be performed using the repetitive movement identified for an element. For example, an element may behave and/or move in a way that is indicative of a specific organ and/or feature. Tracking data of an anticipated rhythmic movement of an element may indicate the organ and/or feature. The determined movement may also be used to improve a perimeter bounding of the element (e.g., as described herein with respect to selection methodology), for example, relative to the background of the video frame. The tracking data may be used to confirm and/or refute the type and/or classification of an element.

Differences in an element between the previous frame 50382 and the current frame 50380 may indicate an outcome associated with the element. For example, an element in the previous frame 50382 and the current frame 50380 may be identified as an organ. The condition of the organ in the previous frame 50382 may be identified as not bleeding, for example. The condition of the organ in the current frame 50380 may be identified as bleeding. The change in conditions from not bleeding to bleeding may indicate a surgical event. The bleeding event may be determined and may be included in the annotation data.

The element identification of the current frame 50392 may be used to further refine and/or update the surgical context data (e.g., as shown at 50396). The further refined and/or updated surgical context data 50396 may be used for element identification, element tracking, and/or verification for a subsequent frame (e.g., such as subsequent frame 50384). For example, the element identification of the subsequent frame may be performed, as shown at 50398. Element tracking and/or verification may be performed (e.g., as shown at 50400) based on the current frame 50380 (e.g., elements from the current frame 50392) and the subsequent frame 50384 (e.g., elements from the subsequent frame 50398).

The tracking data and/or information may be verified, for example, using anticipated tracking information. The anticipated tracking information may be obtained, for example, based on the surgical context data and/or a surgical procedure plan. The annotation data may include an indication that indicates that the elements and/or tracking data is verified. The annotation data may include an indication that indicates that the elements and/or tracking data may need further verification.

Verification may be performed for the identified elements in the video frame(s), for example, based on anticipated tracking information. The anticipated tracking information may be associated with a surgical context (e.g., as indicated by the surgical context data). The anticipated tracking information may be determined, for example, based on the surgical context data, such as by using the surgical procedure plan (e.g., patient-specific surgical procedure plan, as described herein with reference to FIG. 11). For example, a surgical procedure plan may indicate that a surgical instrument is to be used during a surgical step. An element may be verified as a specific surgical instrument, for example, based on the surgical computing system identifying the element as being the specific surgical instrument and the surgical context data indicating that the specific surgical instrument data is proper for the surgical procedure step. The verification may be included in the annotation data. For example, the annotation data may indicate that the identified elements are verified.

Jobs, outcomes, and/or constraints may be determined, for example, for a surgical video. The jobs, outcomes, and/or constraints may be determined based on the surgical context data. Surgical task information associated with a first video frame may be determined using the surgical context data and identified elements in the first video frame. Complication information may be determined associated with the determined surgical task, for example, using the surgical context data, the surgical task information, and the identified elements in the first surgical video frame. Outcome information associated with the surgical task may be determined, for example, based on the surgical context data, the surgical task information, and the complication information.

Jobs, outcomes, and/or constraints may be compiled, for example, for a surgical procedure and/or surgical steps. For example, the annotation data may be used to compile the jobs, outcomes, and/or constraints. The compiled jobs, outcomes, and/or constraints may be used (e.g., with machine learning), for example, to identify issues, change control algorithms and/or parameters, recommend procedural changes for subsequent steps and/or procedures, and/or the like.

Surgical task information may be determined for a video frame in a surgical video. For example, surgical task information may be determined using surgical context data and the identified elements in a video frame. For example, the surgical task information may indicate information associated with the performed surgical task in the video frame. The video frame may be associated with removing a portion of the lungs using a surgical instrument. The surgical task information may include information associated with the surgical instrument used (e.g., type of surgical instrument, surgical instrument parameters, etc.), the time of the removal of the portion of the lungs, and/or the like.

Complication information may be determined for a video frame in the surgical video. For example, the complication information may be determined based on the surgical context data, the surgical task information, and the identified elements in the video frame. The complication information may include information indicating complications detected in the video frame. The complication information may include information indicated possible complications that may occur based on the analysis of the video frame. For example, a video frame may be annotated with information indicating a risk of a complication in subsequent surgical steps in the surgical procedure. The annotation data may indicate the potential complication.

Outcome information may be determined for a video frame in the surgical video. The outcome information may be associated with the surgical task in the video frame. The outcome information may be determined based on the surgical context data, the surgical task information, and the complication information. The outcome information may indicate a likelihood of success for a surgical procedure step. The outcome information may indicate a likely result of the surgical task being performed in the video frame. The outcome information may be used to alter subsequent surgical tasks and/or steps in the surgical procedure.

Change and/or control parameters may be determined for a surgical procedure by analyzing the surgical video frame(s). Change and/or control parameters may be determined, for example, based on the surgical task information, complication information, and/or the outcome information. A determination to change parameters associated with a surgical procedure may be performed. Parameter may include parameters associated with operating a surgical instrument, surgical equipment, and/or the like. Based on a determination to change parameters associated with a surgical procedure, change and/or control parameters may be determined. A control signal may be generated. The control signal may include an indication that indicates the determined control parameters. The control signal may be sent to a surgical control system, for example, that send parameter information to surgical systems (e.g., surgical instruments, surgical equipment, and/or the like). The change and/or control parameters may be used to perform the surgical procedure.

Change parameters for a surgical procedure may be determined based on the annotation data. For example, change parameters may be determined based on the surgical task information, complication information, and/or outcome information. For example, the outcome information may indicate a potential complication for the surgical procedure, for example, if the current parameters were to be used for subsequent surgical tasks and/or steps. The surgical computing system may determine different parameters may be used that are associated with a better surgical outcome (e.g., more efficient procedure, lower risk procedure, and/or better outcome).

The surgical computing system may determine to change parameters associated with performing the surgical procedure. The surgical computing system may determine the change parameters to perform the surgical procedure. The surgical computing system may send a control signal (e.g., indicating the determined control parameters), for example, to a surgical control system. The surgical control system may control the surgical instruments, surgical equipment, and/or the like associated with performing the surgical procedures. The parameters may be adjusted (e.g., automatically adjusted) to use the change parameters indicated in the control signal, for example, by the surgical control system.

Figure 20:
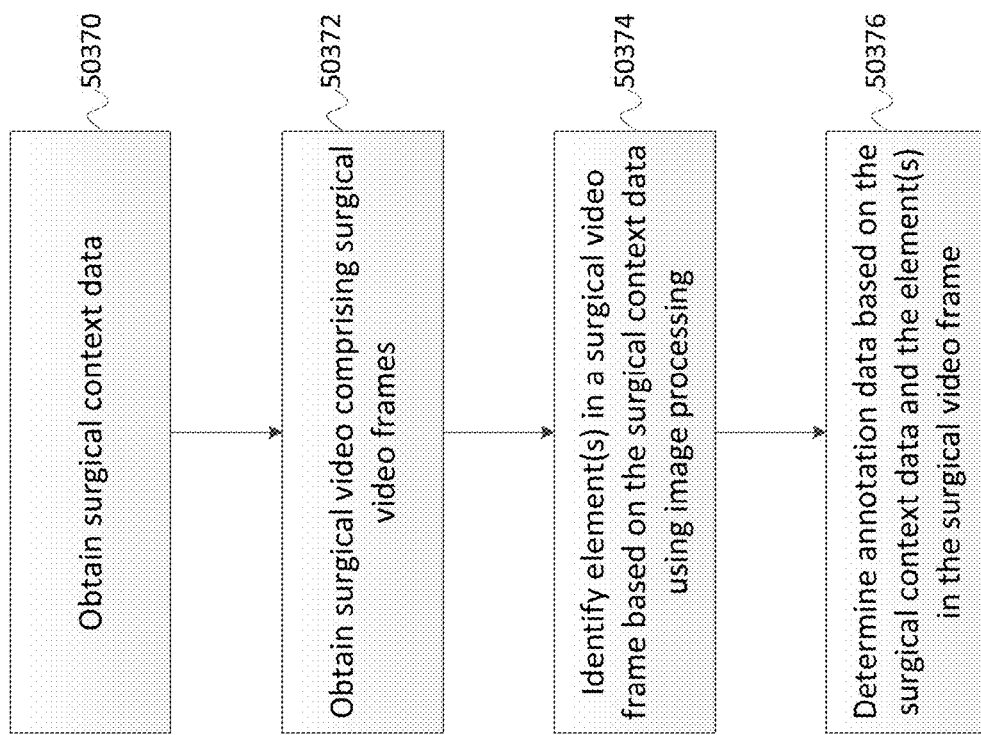
FIG. 20 illustrates an example of generating annotation data into a surgical video using surgical context data and situational awareness.

FIG. 20 illustrates an example flow diagram of generating annotation data associated with a surgical video using surgical context data and situational awareness. As shown, at 50370, surgical context data may be obtained. The surgical context data may be obtained, for example, using surgical procedure data, a surgical procedure plan, and/or the like. As shown at 50372, a surgical video comprising surgical video frames may be obtained. As shown at 50374, element(s) may be identified in a surgical video frame. The element(s) may be identified, for example, based on surgical context data. The element(s) may be identified, for example, using image processing (e.g., as described herein).

As shown at 50376, annotation data may be generated, for example, based on the surgical context data and the element(s) identified in the surgical video frame. For example, the annotation data may include one or more of the following: element identification information, element grouping information, element subgrouping information, element type information, element description information, element condition information, surgical step information, surgical task information, surgical event information, surgical instrument information, surgical equipment information, and/or the like. In some examples, the annotation data may be inserted into the surgical video. The annotation data may be inserted into the video frame. For example, the annotation data may be inserted on a pixel level (e.g., respective annotation data is inserted into each pixel and/or group of pixels). In some examples, the annotation data may be used to generate control signal (e.g., indicating the determined control parameters), for example, to a surgical control system. In some examples, the annotation data may be sent separately from the surgical video (e.g., to a surgical control system, to a surgical analysis system, etc.).

In a surgical procedure, parameters may be used to determine between primary control and confirmation control for a process and/or an operation. For example, a parameter may be monitored in a surgical procedure. An uncertainty associated with the parameter may be determined. The uncertainty associated with the monitored parameter may be used (e.g., as a means) to determine between primary control and confirmation control, for example, of a process and/or operation.

The reliability and/or uncertainty of data from surgical procedure data (e.g., from surgical sensor(s)) may be used, for example, to determine how to perform an automated task. For example, the reliability and/or uncertainty of data from a surgical sensor(s) (e.g., wearables) may be used to determine which of the sensors to use to drive and/or perform an automated task.

The detected reliability and/or uncertainty of the monitored data and/or the magnitude of the uncertainty of a first sensor or detection array and a second detection array may be used, for example, to determine prioritization. For example, the prioritization may be associated with a prioritization of each array in a hierarchy of control of a system or an automated task.

For example, vital organ proximity detection system(s) may analyze the body cavity. An automated task may use a device (e.g., surgical instrument) to move within the body cavity. Sensors may be used, for example, to capture data associated with analyzing the body cavity. Based on the multiple sensors, an autonomous system (e.g., surgical computing system, which may be the surgical hub 20006 as described in FIG. 1) may determine (e.g., using an algorithm) to determine which sensor has the most accurate (e.g., best) proximity measurement (e.g., as compared with the other sensors) for locating the vital organs (e.g., for determining a safe path for the movement, for example, of the surgical instrument in the body cavity). A camera sensor may have a blocked view, but the camera sensor may have tracked the organs and energy device to estimate (e.g., guess) at the locations (e.g., of the vital organs). The device (e.g., surgical instrument in the body cavity) may have an ultrasonic sensor that may locate close objects. The autonomous system may cross reference both sensors (e.g., the camera sensor and the ultrasonic sensor) and determine the safest movement based on the reliability of the data received from the sensors. The organ risk may be considered depending on the device being used to navigate the body cavity. For example, activating an energy device close to the heart is riskier than activating close to the lung.

A surgical job or surgical step may be used to explain (e.g., provide context for) the choices the surgical system may have for controlling the operation, for example, based on multiple (e.g., two) related but differing data streams and a means for determining the reliability of each and how the choices may affect automated control of the process.

A target of uncertainty data may include impendence and/or reflectivity, for example, that may be used to characterize tissue for compression and/or mechanical properties. The impendence and/or reflectivity data may include an unstable measure or a conflicting data element (e.g., less impendence may be related to ore compression). Then, if the data uncertainty exceeds a threshold level, another measure (e.g., reflectivity and/or ultrasonic imaging) may be used as a supplement and/or may replace the use of impendence.

Reliability and/or risk level of an aspect of the surgical procedure may be used, for example, to determine the control reliance on a specific monitored data stream. Automated risk analysis may be performed, for example, to determine a control mechanism reliance on a specific data stream.

Automatic event recording and storage may be performed. For example, device controls may use aggregated intraoperative information from other devices in use in the same surgical procedure.

For example, surgical procedure data may be autonomously collected (e.g., from multiple surgical devices). The surgical procedure data may be aggregated from multiple devices throughout the surgical procedure.

The surgical procedure data may be aggregated throughout the procedure, for example, to predict high level patient and/or tissue factors (e.g., that may influence outcomes associated with other devices used in the surgical procedure). For example, if a surgical procedure data indicates that a patient bleeds more than average (e.g., risk factor), the risk factor may be indicated to other surgical devices to be used in the other surgical devices' algorithms and/or operations. For example, stapling parameter and/or controls (e.g., clamp loads, precomp times, firing speeds, etc.) may be adjusted, for example, based on autonomously collected and interrogated tissue and/or patient information from energy device activations throughout the procedure.

For example, surgical procedure data indicating that energy activations throughout the procedure may have taken longer than typical to ensure an adequate seal. The outcome may be associated with a patient-specific factor, for example, where the patient is more prone to bleed (e.g., as compared to others) and/or does not clot as quickly as normal anatomies. The information may be included and/or used in a stapling algorithm and/or operation. The surgical system may make adjustments to the surgical instrument parameters (e.g., clamp load, precompression time, firing speeds, etc.) to reduce staple line bleeding, for example, if the patient has a higher propensity for bleeding. The surgical hub may recommend a tighter staple than the surgeon may typically use for the procedure.

Surgical device data may be mapped to a location in the patient where the data is being generated. For example, video analysis and/or other markers may be used to track the locations of device usage throughout the procedure, for example, to map the collected device data for future device usage. In examples, during mobilization in a lower anterior resection (LAR), an energy transection near the rectum may provide data that indicates lower relative tissue perfusion and/or lower relative likelihood for the staple line to bleed in that area. In examples, in the same procedure, an energy transection up the colon may be more perfuse and may be more likely to ooze. To limit intra-operative bleeding, staple controls and reload selection may be different at each location. The surgical system may track the energy activations by location and may track the position of endocutter firings. If the endocutter is in close proximity to where a given energy activation was completed, the endocutter controls and/or parameters may be adjusted accordingly.

The surgical system may track device data. For example, visible bleeding from video analysis may be determined. Energy device tissue sealing data (e.g., time to seal and/or complete a transection) may be obtained and/or determined. Perfusion measures may be determined. Tissue load curves from various device clamping may be used to determine density and/or perform viscoelasticity analysis. Tissue fluid content may be determined, for example, based on impendence (e.g., from energy devices).

A surgeon may actively request tissue information. An energy device tissue interrogation mode may be used to detect tissue thickness and/or condition for use in stapling. Feedback may be given to the surgeon and support cartridge selection and/or directly apply information to compression and/or firing algorithms.

For example, a surgeon may activate the tissue interrogation mode on a bipolar device prior to transecting with a stapler. The bipolar device may go into a non-therapeutic energy delivery mode. The surgeon may clamp and release on the intended staple line transection are, for example, while the non-therapeutic energy passes between the jaws. The impendence and/or other energy data may be used to estimate tissue thickness. The surgical system may communicate the estimated tissue thickness and recommend staple reload parameters to the surgeon. The data recorded from the tissue interrogation may be used a part of the stapling compression and/or firing algorithm, for example, if the surgeon uses the stapler. Bipolar devices may use impedance as a predictor. Harmonic devices may use ultra-low energy mode. Tissue resistance, density, vibration response, and/or the like may be used as a predictor (e.g., by harmonic devices). Stapling algorithms may be adjusted based on energy device feedback to determine tissue type, thickness, density, condition, and/or the like. Energy device feedback may be used to confirm tumor margins prior to stapling.

Event and/or situational relevance may be determined for a surgical procedure, for example, to control automatic storage of an event and timing. Relevance, risk, and/or criticality of a task may be used to determined, for example, if, when, where, and/or how often the aspects of the situation and/or event are stored.

Motion sensing may be used, for example, instead of frame to frame comparison, for example for automatic event recording and/or storage. Event based cameras may be used. Identification and re-identification of objects in combination with a memory of key and/or common object previous placement may be performed to allow for the object location to be stored. The stored coordinated system may be adjusted, for example, as the object is moved, for example, to free up inter-frame comparison of pixels and images for systems that have a stationary, fixed, and/or predefined location. The amount of image processing on portions of the system view that are less consequential (e.g., but object location still matters), may be limited.

The invention claimed is:

1. A computing system comprising:
a processor configured to:
obtain surgical context data;
obtain a surgical video comprising one or more surgical video frames;
identify one or more elements in a first surgical video frame based on the obtained surgical context data using image processing, wherein the one or more elements comprise a respective group of pixels associated with the first surgical video frame;
generate first annotation data for the first surgical video frame based on the surgical context data and the one or more elements in the first surgical video frame, wherein the first annotation data comprises respective element annotation data associated with the identified one or more elements in the first surgical video frame;
determine an anticipated movement associated with the one or more elements in the first surgical video frame based at least on the surgical context data;
identify the one or more elements in a second surgical video frame based on the obtained surgical context data using image processing, wherein the one or more elements comprise a respective group of pixels associated with the second surgical video frame, wherein the identification of the one or more elements in the second surgical video frame is verified based on the determined anticipated movement associated with the one or more elements in the first surgical video frame; and
generate second annotation data for the second surgical video frame based on the surgical context data and the one or more elements in the second surgical video frame.

2. The computing system of claim 1, wherein the processor is further configured to:
insert the first annotation data for the first surgical video frame into the surgical video, wherein the respective element annotation data is attached to the respective group of pixels.

3. The computing system of claim 1, wherein the processor is further configured to:
identify a plurality of sub-elements associated with a first element identified in the first surgical video frame based on the surgical context data using image processing, wherein a sub-element comprises a respective subgroup of pixels, wherein the element annotation data comprises respective sub-element annotation data associated with the plurality of sub-elements; and
attach the respective sub-element annotation data to the respective subgroup of pixels.

4. The computing system of claim 1, wherein the first annotation data comprises one or more of element identification information, element grouping information, element subgrouping information, element type information, element description information, element condition information, surgical step information, surgical task information, surgical event information, surgical instrument information, or surgical equipment information.

5. The computing system of claim 1, wherein the processor is further configured to:
refine the surgical context data based on the identified one or more elements in the first surgical video frame, wherein the one or more elements in the second surgical video frame is further identified based on the refined surgical context data using image processing, and wherein the second annotation data for the second surgical video frame is further generated based on the refined surgical context data.

6. The computing system of claim 1, wherein the processor is further configured to:
determine tracking data for the second surgical video frame based on the one or more elements in the first surgical video frame and the one or more elements in the second video frame, wherein the tracking data is associated with one or more of an element behavior, an element movement, or outcome information, wherein the second annotation data comprises the tracking data for the second surgical video frame.

7. The computing system of claim 1, wherein the anticipated tracking information is further determined based on a surgical procedure plan.

8. The computing system of claim 1, wherein the processor is further configured to:
determine surgical task information associated with the first surgical video frame using the surgical context data and the identified one or more elements in the first surgical video frame; and
generate control parameters for the surgical procedure based on the determined surgical task information; and
send a control signal comprising an indication that indicates the determined control parameters to a surgical control system.

9. The computing system of claim 1, wherein the processor is further configured to:
determine surgical task information associated with the first surgical video frame using the surgical context data and the identified one or more elements in the first surgical video frame;
determine complication information associated with the determined surgical task using the surgical context data, the surgical task information, and the identified one or more elements in the first surgical video frame;
generate control parameters for the surgical procedure based on the determined complication information; and
send a control signal comprising an indication that indicates the determined control parameters to a surgical control system.

10. The computing system of claim 1, wherein the processor is further configured to:
determine surgical task information associated with the first surgical video frame using the surgical context data and the identified one or more elements in the first surgical video frame;
determine complication information associated with the determined surgical task using the surgical context data, the surgical task information, and the identified one or more elements in the first surgical video frame;
determine outcome information associated with the surgical task based on the surgical context data, the surgical task information, and the complication information;
determine to change parameters associated with the surgical procedure based on the surgical task information, complication information, and the outcome information;
based on the determination to change parameters, generate control parameters for the surgical procedure; and
send a control signal to a surgical control system comprising an indication that indicates the determined control parameters.

11. A method comprising:
obtaining surgical context data;
obtaining a surgical video comprising one or more surgical video frames;
identifying one or more elements in a first surgical video frame based on the obtained surgical context data using image processing, wherein the one or more elements comprise a respective group of pixels associated with the first surgical video frame;
generating first annotation data for the first surgical video frame based on the surgical context data and the one or more elements in the first surgical video frame, wherein the first annotation data comprises respective element annotation data associated with the identified one or more elements in the first surgical video frame;
determining an anticipated movement associated with the one or more elements in the first surgical video frame based at least on the surgical context data;
identifying the one or more elements in a second surgical video frame based on the obtained surgical context data using image processing, wherein the one or more elements comprise a respective group of pixels associated with the second surgical video frame, wherein the identification of the one or more elements in the second surgical video frame is verified based on the determined anticipated movement associated with the one or more elements in the first surgical video frame; and
generating second annotation data for the second surgical video frame based on the surgical context data and the one or more elements in the second surgical video frame.

12. The method of claim 11, further comprising:
inserting the first annotation data for the first surgical video frame into the surgical video, wherein the respective element annotation data is attached to the respective group of pixels.

13. The method of claim 11, further comprising:
identifying a plurality of sub-elements associated with a first element identified in the first surgical video frame based on the surgical context data using image processing, wherein a sub-element comprises a respective subgroup of pixels, wherein the element annotation data comprises respective sub-element annotation data associated with the plurality of sub-elements; and
attaching the respective sub-element annotation data to the respective subgroup of pixels.

14. The method of claim 11, wherein the first annotation data comprises one or more of element identification information, element grouping information, element subgrouping information, element type information, element description information, element condition information, surgical step information, surgical task information, surgical event information, surgical instrument information, or surgical equipment information.

15. The method of claim 11, further comprising:
refining the surgical context data based on the identified one or more elements in the first surgical video frame, wherein the one or more elements in the second surgical video frame is further identified based on the refined surgical context data using image processing, and wherein the second annotation data for the second surgical video frame is further generated based on the refined surgical context data.

16. The method of claim 11, further comprising:
determining tracking data for the second surgical video frame based on the one or more elements in the first surgical video frame and the one or more elements in the second video frame, wherein the tracking data is associated with one or more of an element behavior, an element movement, or outcome information; and
wherein the second annotation data comprises the tracking data for the second surgical video frame.

17. The method of claim 11, further comprising:
determining surgical task information associated with the first surgical video frame using the surgical context data and the identified one or more elements in the first surgical video frame;
determining complication information associated with the determined surgical task using the surgical context data, the surgical task information, and the identified one or more elements in the first surgical video frame;
determining outcome information associated with the surgical task based on the surgical context data, the surgical task information, and the complication information;
determining to change parameters associated with the surgical procedure based on the surgical task information, complication information, and the outcome information;
based on the determination to change parameters, generate control parameters for the surgical procedure; and
sending a control signal to a surgical control system comprising an indication that indicates the determined control parameters.

18. A non-transitory computer-readable medium comprising instructions which, when executed by a processor, cause the processor to:
obtain surgical context data;
obtain a surgical video comprising one or more surgical video frames;
identify one or more elements in a first surgical video frame based on the obtained surgical context data using image processing, wherein the one or more elements comprise a respective group of pixels associated with the first surgical video frame;
generate first annotation data for the first surgical video frame based on the surgical context data and the one or more elements in the first surgical video frame, wherein the first annotation data comprises respective element annotation data associated with the identified one or more elements in the first surgical video frame;
determine an anticipated movement associated with the one or more elements in the first surgical video frame based at least on the surgical context data;
identify the one or more elements in a second surgical video frame based on the obtained surgical context data using image processing, wherein the one or more elements comprise a respective group of pixels associated with the second surgical video frame, wherein the identification of the one or more elements in the second surgical video frame is verified based on the determined anticipated movement associated with the one or more elements in the first surgical video frame; and
generate second annotation data for the second surgical video frame based on the surgical context data and the one or more elements in the second surgical video frame.

* * * * *